(12) United States Patent
Noordin et al.

(10) Patent No.: US 10,060,922 B2
(45) Date of Patent: Aug. 28, 2018

(54) IN VIVO INDUCED TOXOPLASMA GONDII PROTEIN FOR APPLICATION IN DIAGNOSIS, VACCINE AND THERAPY

(71) Applicant: Universiti Sains Malaysia, Pulau Pinang (MY)

(72) Inventors: Rahmah Binti Noordin, Pulau Pinang (MY); Atefeh Amerizadeh, Pulau Pinang (MY)

(73) Assignee: UNIVERSITI SAINS MALAYSIA, Pulau Pinang (MY)

( * ) Notice: Subject to any disclaimer, the term of this patent is extended or adjusted under 35 U.S.C. 154(b) by 0 days.

(21) Appl. No.: 15/519,150

(22) PCT Filed: Oct. 1, 2015

(86) PCT No.: PCT/IB2015/057522
§ 371 (c)(1),
(2) Date: Apr. 13, 2017

(87) PCT Pub. No.: WO2016/059502
PCT Pub. Date: Apr. 21, 2016

(65) Prior Publication Data
US 2017/0234872 A1    Aug. 17, 2017

(30) Foreign Application Priority Data

Oct. 16, 2014 (MY) ............................ PI2014002940

(51) Int. Cl.
| | | |
|---|---|---|
| *A61K 39/012* | (2006.01) | |
| *A61K 39/00* | (2006.01) | |
| *G01N 33/53* | (2006.01) | |
| *G01N 33/569* | (2006.01) | |
| *A61K 39/002* | (2006.01) | |

(52) U.S. Cl.
CPC ..... *G01N 33/56905* (2013.01); *A61K 39/002* (2013.01); *G01N 2333/45* (2013.01); *G01N 2469/20* (2013.01)

(58) Field of Classification Search
CPC .............................. A61K 39/00; A61K 39/395
USPC ..... 424/9.1, 9.2, 184.1, 185.1, 234.1, 273.1; 435/4, 6.1, 7.1; 536/23.1, 23.7
See application file for complete search history.

(56) References Cited

PUBLICATIONS

Antibodies-Online Inc. "Thyroglobulin (TG) protein (His tag)," Accessible on the Internet at URL: http://www.proteogenix-antibody.com/prod-Recombinant_Protein-RAP_domain_containing_protein,PX-P2097-10.html [Last Accessed Feb. 26, 2016].
Kotresha et al. (2010) "Recombinant proteins in the diagnosis of toxoplasmosis," APMIS. 118:529-542.
Igarshi et al. (2008) "Toxoplasma gondii: humoral and cellular immune response of BALB/c mice immunized via intranasal route with rTgROP2," Genetics and Molecular Research. 7:305-313.
Proteogenix "RAP Domain-Containing Protein," Catalog No. PX-P2097-10. Accessible on the Internet at URL: http://proteogenix-antibody.com/prod-Recombinant_Protein-RAP_domain_containing_protein,PX-)2097-10.html [Last Accessed Feb. 26, 2016].
Uniprot Database [Online] (Oct. 16, 2013) "UniProtKB—S8EY82 (S8EY82_TOXGM)," Accession No. S8EY82. UniProt Consortium. Accessible on the Internet at URL: http://www.uniprot.org/uniprot/S8EY82. [Last Accessed Feb. 26, 2016].
International Search Report with Written Opinion corresponding to International Patent Application No. PCT/IB2015/057522, dated Feb. 8, 2016.

*Primary Examiner* — Rodney P Swartz
(74) *Attorney, Agent, or Firm* — Lathrop Gage LLP; Brian C. Thrinque

(57) ABSTRACT

The present invention relates to methods of screening biological samples for the presence of *T. gondii*. More particularly, the present invention relates to a sensitive and specific screening test for the presence of Toxoplasmosis in subjects by using or detecting the in vivo-induced *T. gondii* RAP domain binding protein antigen. The invention further relates to the use of the in vivo-induced antigen in the prevention or therapy of Toxoplasmosis.

8 Claims, 8 Drawing Sheets
Specification includes a Sequence Listing.

SEQ ID NO: 1

```
AGAAGCGTAC   GCGAGCAATA   TAATGCATCT   GAAGTTGATC   CGGGAGAAAA
CAGCGCCACG   GGTGGAGGAG   TTGGAGACCC   TTTTCTCGGA   AACAAGAGGG
AGAATAATAC   TTCATTTAAG   GTTCTTGAAT   CCCGGTCTGT   ATGCACACCC
GAGGAATTGA   GGCGTCGGTC   GACTCTGTTA   ACGACCATCT   TACGCACTCT
GTCTCGCAGT   TCCCTGAGGC   GCCATCCACT   TAACTCGCCG   TTCGAACGCG
CGTGGAGACA   GCTGAAAATT   ATCGACCTGT   ATCTTCAGTT   CAATGTAGGA
CCTCTGCGTG   TAGATGATGA   GGAAGCGCTT   CAGTTTCTGT   CTCTTGCTCG
GACGAAGAAG   CTATTGAACC   TGGTTCATGT   GTCCCAGGTA   CAGAAGCGT   399
nucleotides
```

FIGURE 2

SEQ ID NO: 2

```
Arg Ser Val Arg Glu Gln Tyr Asn Ala Ser Glu Val Asp Pro Gly Glu
1               5                   10                  15
Asn Ser Ala Thr Gly Gly Gly Val Gly Asp Pro Phe Leu Gly Asn Lys
                20                  25                  30
Arg Glu Asn Asn Thr Ser Phe Lys Val Leu Glu Ser Arg Ser Val Cys
                35                  40                  45
Thr Pro Glu Glu Leu Arg Arg Arg Ser Thr Leu Leu Thr Thr Ile Leu
    50                  55                  60
Arg Thr Leu Ser Arg Ser Ser Leu Arg Arg His Pro Leu Asn Ser Pro
65                  70                  75                  80
Phe Glu Arg Ala Trp Arg Gln Leu Lys Ile Ile Asp Leu Tyr Leu Gln
                85                  90                  95
Phe Asn Val Gly Pro Leu Arg Val Asp Asp Glu Glu Ala Leu Gln Phe
                100                 105                 110
Leu Ser Leu Ala Arg Thr Lys Lys Leu Leu Asn Leu Val His Val Ser
            115                 120                 125
Gln Val Gln Lys Arg
    130
```

FIGURE 3

SEQ ID NO: 3

```
ATGAAGTCGCATTCCAGACTACGGAAACTTGCGTCCGCAGTACAGACACCGCGGCCTTTT
AGACGGACAGTCCGAGACGGCCACCGGCACGAGTGTTTTTCTGCGACCCCTACCGCGAC
GCTGAAGTCGCTTTTTCTCCAGAGGAGCGAGCAACCGAGGGTCACGTGTCTGCTTCACGC
GAATCCAACAGTTTCAGACAGTTCGTGGAGTTGTCGACGCTGCCACGTGGAGTCAGGCCG
AGTGCCCCCAGGCTTCTCCACCATACACTGGAAGTCGGCGACTCCCGCCACGCGTCACAG
CGGTCTTCCCATGTCTTCTACCGCAACTCGTTGTCTGGACTGTCAGGAATCAACGCAGTG
ACTTCTTTTGCAAGCTGGAAACCTCCTTCGGTCATCCCACTATTTTCTGCAAGAGACGGA
CGTTTCGCCCACAGCAGCTGTTTGCGTGCTGGTCCAGGGCACTTCGTCGAGACCGCACAG
GTTGGAGATGGAGGAGAGAGGGAGGCCGTGCTTTCCGCTGGGGCTGGGGACGCCCGTCCA
GCTGAGGAACGGCAGGCAGAAGAGCCTGTGAAGCATCTGGGGGATGCCGAAGAAGTTGCC
TTAGACACGCGCGTCTTCGACGAGTGTGTCTACACAGAGGACGAGGATATTTTGGAGAAG
AAACGGAGGATTGGCGTGGGAATGAGAGTCGGGGGTTCAGCGCCACATCGTCGCGGCGCT
TCCTTCTCTCCCTCCCTGTCGCCAGATCCGCCTTTTTCCTCTTCTGACCTTCCGGACTCC
TTTCCTTTTACGCTTTCCTCGCAGTGTCCGCGTCCCGACTCCCTTCCTCCGTCTCCGCCG
CACGGCGCGCCCTTCTCTCCGACATGCGCGCCTTCTTCTGCGCTGTCCTCGTCGCCTAAA
CTTGTCCCAGTCTCCGAGTACCGCAAACGGTCGTTGCGGTTTCCTCCGGACCAGGTGGCG
GTGGGAGCTTTTGAGTTGGCGGTAAAATTCGAGACTCTCGTATCCCTTCGTTTCCCTCTC
GACCAGCACCCGCGAAGAGCGCAGCCCGGCTCTCGCTCTCAGCCTTCTTCTCTCGCCTCC
TCCCGTCCCCTCGCTGAGATGCCCCAGCCATACGGCAGCCTCCCTCCGCCGGTGGCTTTC
GAGAAGATGCTCGGCGACGCCATTTCGACTACCAAAGCCAATGCAGACATCTTGCCTGTG
TCGACACTGCTCTCTGTCGCTCATGCAGCTGCGCGGCTGGGGGTGCAGGTTTTTTCCTTC
GCCTCGGCTCTCCGGCGCCGCGCCCTAGTGCTTCTTCCTGAAATAAAGAATCCCGCGGCC
TTCATCCGGCTCCTGCAAGACTTGGAGAAGTTGGGAGGTCTGGGCGACCGCCACTTTGTC
TTCTTCAGAGAGAAAGTAAAGGAGACGCTCCAGAGCGCTTCTTCACGCTGCTCGCTGTTC
GGGACCGCACTGGTCGTTCACCTCCTCGCTCGACACAGATTGCGAGACGAGGAACTCCTC
ACTCTCGCGTACCGCAGGTTTTCGAGAAATCGATACACTCTCGCTGCAGCTGTGAGACAA
ACGCCTTCTCCTGGCGGCGCTGCCGCTGGCACTGTCGCGGCTCGAGGTCCCTACGCTG
GCTGCAGCGGTGTTGGACAGTCTGCTCAGTGACCAGGCGCCAGCAGCTGTCAGTCAGTTG
TCGATTCACGAACTGTCAAACCTTGCTTATGCAATCGCATGCGTCTCCACCAATTCCCAA
GTTACTGTAGACACGCATCCGTCCTCTGCGGACTCAGGCTCTTGTCATGAGCAGAGGCCG
GAGCGTTTCGAGGTTGGTTCATCGGAAAAGGAGTGTCAGTCTGGGATGAAGATGCAACTG
CATCCGGAGCATAGAAGCGTACGCGAGCAATATAATGCATCTGAAGTTGATCCGGGAGAA
AACAGCGCCACGGGTGGAGGAGTTGGAGACCCTTTTCTCGGAAACAAGAGGGAGAATAAT
ACTTCATTTAAGGTTCTTGAATCCCGGTCTGTATGCACACCCGAGGAATTGAGGCGTCGG
TCGACTCTGTTAACGACCATCTTACGCACTCTGTCTCGCAGTTCCCTGAGGCGCCATCCA
CTTAACTCGCCGTTCGAACGCGCGTGGAGACAGCTGAAAATTATCGACCTGTATCTTCAG
TTCAATGTAGGACCTCTGCGTGTAGATGATGAGGAAGCGCTTCAGTTTCTGTCTCTTGCT
CGGACGAAGAAGCTATTGAACCTGGTTCATGTGTCCCAGGTACAGAAGCGTGTTGGGCGC
TTGCTTTTCGATGAAGGACTGATGTCTGAAATAGACGTTGAGTACCCACTGGGGCCTTAC
GTCTTAGACTTTGCAATACCGTCTCGCAAGCTTGTTGTAGAAGTTGATGGGGAAGCCCAT
TTCTTCTTTGGTACAACGGTGCCAACTGCTCAGACGCGAATGAAGCGCGAACTGCTTGCC
GCTATGGGGTGGCGCGTGGTCGTCGTTCCGCAGGAACTTTGGAGAAATAAAAGGAAAGGG
AAAATTAAAGAATTCGTGGCGAGAAAGGTGCGAGAGGGACTCGAGATCGACAACAGTGAC
AGATAG 2586
```

FIGURE 4

SEQ ID NO: 4

```
MKSHSRLRKL ASAVQTPRPF RRTVRDGHRH ECFSATPYRD AEVAFSPEER ATEGHVSASR
ESNSFRQFVE LSTLPRGVRP SAPRLLHHTL EVGDSRHASQ RSSHVFYRNS LSGLSGINAV
TSFASWKPPS VIPLFSARDG RFAHSSCLRA GPGHFVETAQ VGDGGEREAV LSAGAGDARP
AEERQAEEPV KHLGDAEEVA LDTRVFDECV YTEDEDILEK KRRIGVGMRV GGSAPHRRGA
SFSPSLSPDP PFSSSDLPDS FPFTLSSQCP RPDSLPPSPP HGAPFSPTCA PSSALSSSPK
LVPVSEYRKR SLRFPPDQVA VGAFELAVKF ETLVSLRFPL DQHPRRAQPG SRSQPSSLAS
SRPLAEMPQP YGSLPPPVAF EKMLGDAIST TKANADILPV STLLSVAHAA ARLGVQVFSF
ASALRRRALV LLPEIKNPAA FIRLLQDLEK LGGLGDRHFV FFREKVKETL QSASSRCSLF
GTALVVHLLA RHRLRDEELL TLAYRRFSRN RYTLAAAVRQ TPSLLAALPL ALSRLEVPTL
AAAVLDSLLS DQAPAAVSQL SIHELSNLAY AIACVSTNSQ VTVDTHPSSA DSGSCHEQRP
ERFEVGSSEK ECQSGMKMQL HPEHRSVREQ YNASEVDPGE NSATGGGVGD PFLGNKRENN
TSFKVLESRS VCTPEELRRR STLLTTILRT LSRSSLRRHP LNSPFERAWR QLKIIDLYLQ
FNVGPLRVDD EEALQFLSLA RTKKLLNLVH VSQVQKRVGR LLFDEGLMSE IDVEYPLGPY
VLDFAIPSRK LVVEVDGEAH FFFGTTVPTA QTRMKRELLA AMGWRVVVVP QELWRNKRKG
KIKEFVARKV REGLEIDNSDR
```
Sequence Length: 861 amino acids

FIGURE 5

Representative immunoblot results of rTgRA15 antigen incubated with individual negative and positive serum samples Strip M     : low molecular weight, unstained marker Strips 1-3  : IgG- IgM-, serum samples from healthy people Strip 4     : positive control Strip 5     : negative control Strip 6     : IgM+ IgG+, low IgG avidity (acute serum sample)

Strips 7-8  : IgG+ IgM- (chronic serum samples)

Negative    Positive    Strong positive

SEQUENCE LISTING

```
<160> NUMBER OF SEQ ID NOS: 8

<210> SEQ ID NO 1
<211> LENGTH: 399
<212> TYPE: DNA
<213> ORGANISM: Toxoplasma gondii
<220> FEATURE:
<221> NAME/KEY: RAPdomainbindingproteinAM15clone
<222> LOCATION: (1)..(399)

<400> SEQUENCE: 1
agaagcgtac gcgagcaata taatgcatct gaagttgatc cgggagaaaa cagcgccacg      60
ggtggaggag ttggagaccc ttttctcgga aacaagaggg agaataatac ttcatttaag     120
gttcttgaat cccggtctgt atgcacaccc gaggaattga ggcgtcggtc gactctgtta     180
acgaccatct tacgcactct gtctcgcagt tccctgaggc gccatccact taactcgccg     240
ttcgaacgcg cgtggagaca gctgaaaatt atcgacctgt atcttcagtt caatgtagga     300
cctctgcgtg tagatgatga ggaagcgctt cagtttctgt ctcttgctcg gacgaagaag     360
ctattgaacc tggttcatgt gtcccaggta cagaagcgt                             399

<210> SEQ ID NO 2
<211> LENGTH: 133
<212> TYPE: PRT
<213> ORGANISM: Toxoplasma gondii
<220> FEATURE:
<221> NAME/KEY: rTgRA15aminoacid
<222> LOCATION: (1)..(133)

<400> SEQUENCE: 2

Arg Ser Val Arg Glu Gln Tyr Asn Ala Ser Glu Val Asp Pro Gly Glu
1               5                   10                  15

Asn Ser Ala Thr Gly Gly Gly Val Gly Asp Pro Phe Leu Gly Asn Lys
            20                  25                  30

Arg Glu Asn Asn Thr Ser Phe Lys Val Leu Glu Ser Arg Ser Val Cys
        35                  40                  45

Thr Pro Glu Glu Leu Arg Arg Arg Ser Thr Leu Leu Thr Thr Ile Leu
    50                  55                  60

Arg Thr Leu Ser Arg Ser Ser Leu Arg Arg His Pro Leu Asn Ser Pro
65                  70                  75                  80
```

```
Phe Glu Arg Ala Trp Arg Gln Leu Lys Ile Ile Asp Leu Tyr Leu Gln
                85                  90                  95

Phe Asn Val Gly Pro Leu Arg Val Asp Asp Glu Ala Leu Gln Phe
            100                 105                 110

Leu Ser Leu Ala Arg Thr Lys Lys Leu Leu Asn Leu Val His Val Ser
        115                 120                 125

Gln Val Gln Lys Arg
    130

<210> SEQ ID NO 3
<211> LENGTH: 2586
<212> TYPE: DNA
<213> ORGANISM: Toxoplasma gondii
<220> FEATURE:
<221> NAME/KEY: RAPdomainbindingproteinDNAcoding
<222> LOCATION: (1)..(2586)

<400> SEQUENCE: 3
```

| | | | | |
|---|---|---|---|---|
| atgaagtcgc | attccagact | acggaaactt | gcgtccgcag | tacagacacc gcggcctttt | 60 |
| agacggacag | tccgagacgg | ccaccggcac | gagtgttttt | ctgcgacccc ctaccgcgac | 120 |
| gctgaagtcg | cttttctcc | agaggagcga | gcaaccgagg | gtcacgtgtc tgcttcacgc | 180 |
| gaatccaaca | gtttcagaca | gttcgtggag | ttgtcgacgc | tgccacgtgg agtcaggccg | 240 |
| agtgccccca | ggcttctcca | ccatacactg | gaagtcggcg | actccgcca cgcgtcacag | 300 |
| cggtcttccc | atgtcttcta | ccgcaactcg | ttgtctggac | tgtcaggaat caacgcagtg | 360 |
| acttcttttg | caagctggaa | acctccttcg | gtcatcccac | tattttctgc aagagacgga | 420 |
| cgtttcgccc | acagcagctg | tttgcgtgct | ggtccagggc | acttcgtcga ccgcacag | 480 |
| gttggagatg | gaggagagag | ggaggccgtg | ctttccgctg | ggctggga cgcccgtcca | 540 |
| gctgaggaac | ggcaggcaga | agagcctgtg | aagcatctgg | gggatgccga agaagttgcc | 600 |
| ttagacacgc | gcgtcttcga | cgagtgtgtc | tacacagagg | acgaggatat tttggagaag | 660 |
| aaacggagga | ttggcgtggg | aatgagagtc | gggggttcag | cgccacatcg tcgcggcgct | 720 |
| tccttctctc | cctccctgtc | gccagatccg | cctttttcct | cttctgacct tccggactcc | 780 |
| tttcctttta | cgctttcctc | gcagtgtccg | cgtcccgact | cccttcctcc gtctccgccg | 840 |
| cacggcgcgc | ccttctctcc | gacatgcgcg | ccttcttctg | cgctgtcctc gtcgcctaaa | 900 |
| cttgtcccag | tctccgagta | ccgcaaacgg | tcgttgcggt | ttcctccgga ccaggtggcg | 960 |
| gtgggagctt | tgagttggc | ggtaaaattc | gagactctcg | tatcccttcg tttccctctc | 1020 |
| gaccagcacc | cgcgaagagc | gcagcccggc | tctcgctctc | agccttcttc tctcgcctcc | 1080 |
| tcccgtcccc | tcgctgagat | gccccagcca | tacggcagcc | tccctccgcc ggtggctttc | 1140 |
| gagaagatgc | tcggcgacgc | catttcgact | accaaagcca | atgcagacat cttgcctgtg | 1200 |
| tcgacactgc | tctctgtcgc | tcatgcagct | gcgcggctgg | gggtgcaggt ttttccttc | 1260 |
| gcctcggctc | tccggcgccg | cgccctagtg | cttcttcctg | aaataaagaa tcccgcggcc | 1320 |
| ttcatccggc | tcctgcaaga | cttggagaag | ttgggaggtc | tgggcgaccg ccactttgtc | 1380 |
| ttcttcagag | agaaagtaaa | ggagacgctc | cagagcgctt | cttcacgctg ctcgctgttc | 1440 |
| gggaccgcac | tggtcgttca | cctcctcgct | cgacacagat | gcgagacga ggaactcctc | 1500 |
| actctcgcgt | accgcaggtt | ttcgagaaat | cgatacactc | tcgctgcagc tgtgagacaa | 1560 |
| acgccttctc | tcctggcggc | gctgccgctg | gcactgtcgc | ggctcgaggt ccctacgctg | 1620 |
| gctgcagcgg | tgttggacag | tctgctcagt | gaccaggcgc | cagcagctgt cagtcagttg | 1680 |

-continued

```
tcgattcacg aactgtcaaa ccttgcttat gcaatcgcat gcgtctccac caattcccaa    1740
gttactgtag acacgcatcc gtcctctgcg gactcaggct cttgtcatga gcagaggccg    1800
gagcgtttcg aggttggttc atcggaaaag gagtgtcagt ctgggatgaa gatgcaactg    1860
catccggagc atagaagcgt acgcgagcaa tataatgcat ctgaagttga tccgggagaa    1920
aacagcgcca cgggtggagg agttggagac cctttctcg gaaacaagag ggagaataat    1980
acttcattta aggttcttga atcccggtct gtatgcacac ccgaggaatt gaggcgtcgg    2040
tcgactctgt taacgaccat cttacgcact ctgtctcgca gttccctgag gcgccatcca    2100
cttaactcgc cgttcgaacg cgcgtggaga cagctgaaaa ttatcgacct gtatcttcag    2160
ttcaatgtag gacctctgcg tgtagatgat gaggaagcgc ttcagtttct gtctcttgct    2220
cggacgaaga agctattgaa cctggttcat gtgtcccagg tacagaagcg tgttgggcgc    2280
ttgcttttcg atgaaggact gatgtctgaa atagacgttg agtacccact ggggccttac    2340
gtcttagact ttgcaatacc gtctcgcaag cttgttgtag aagttgatgg ggaagcccat    2400
ttcttctttg gtacaacggt gccaactgct cagacgcgaa tgaagcgcga actgcttgcc    2460
gctatggggt ggcgcgtggt cgtcgttccg caggaacttt ggagaaataa aaggaaaggg    2520
aaaattaaag aattcgtggc gagaaaggtg cgagagggac tcgagatcga caacagtgac    2580
agatag                                                                2586
```

<210> SEQ ID NO 4
<211> LENGTH: 861
<212> TYPE: PRT
<213> ORGANISM: Toxoplasma gondii
<220> FEATURE:
<221> NAME/KEY: RAPdomainbindingprotein
<222> LOCATION: (1)..(861)

<400> SEQUENCE: 4

Met Lys Ser His Ser Arg Leu Arg Lys Leu Ala Ser Ala Val Gln Thr
1               5                   10                  15

Pro Arg Pro Phe Arg Arg Thr Val Arg Asp Gly His Arg His Glu Cys
            20                  25                  30

Phe Ser Ala Thr Pro Tyr Arg Asp Ala Glu Val Ala Phe Ser Pro Glu
        35                  40                  45

Glu Arg Ala Thr Glu Gly His Val Ser Ala Ser Arg Glu Ser Asn Ser
    50                  55                  60

Phe Arg Gln Phe Val Glu Leu Ser Thr Leu Pro Arg Gly Val Arg Pro
65                  70                  75                  80

Ser Ala Pro Arg Leu Leu His His Thr Leu Glu Val Gly Asp Ser Arg
                85                  90                  95

His Ala Ser Gln Arg Ser Ser His Val Phe Tyr Arg Asn Ser Leu Ser
            100                 105                 110

Gly Leu Ser Gly Ile Asn Ala Val Thr Ser Phe Ala Ser Trp Lys Pro
        115                 120                 125

Pro Ser Val Ile Pro Leu Phe Ser Ala Arg Asp Gly Arg Phe Ala His
    130                 135                 140

Ser Ser Cys Leu Arg Ala Gly Pro Gly His Phe Val Glu Thr Ala Gln
145                 150                 155                 160

Val Gly Asp Gly Gly Glu Arg Glu Ala Val Leu Ser Ala Gly Ala Gly
                165                 170                 175

Asp Ala Arg Pro Ala Glu Glu Arg Gln Ala Glu Glu Pro Val Lys His
            180                 185                 190

```
Leu Gly Asp Ala Glu Glu Val Ala Leu Asp Thr Arg Val Phe Asp Glu
    195                 200                 205

Cys Val Tyr Thr Glu Asp Asp Ile Leu Glu Lys Lys Arg Arg Ile
210                 215                 220

Gly Val Gly Met Arg Val Gly Gly Ser Ala Pro His Arg Arg Gly Ala
225                 230                 235                 240

Ser Phe Ser Pro Ser Leu Ser Pro Asp Pro Phe Ser Ser Asp
                    245                 250                 255

Leu Pro Asp Ser Phe Pro Phe Thr Leu Ser Ser Gln Cys Pro Arg Pro
                260                 265                 270

Asp Ser Leu Pro Pro Ser Pro Pro His Gly Ala Pro Phe Ser Pro Thr
            275                 280                 285

Cys Ala Pro Ser Ser Ala Leu Ser Ser Ser Pro Lys Leu Val Pro Val
290                 295                 300

Ser Glu Tyr Arg Lys Arg Ser Leu Arg Phe Pro Pro Asp Gln Val Ala
305                 310                 315                 320

Val Gly Ala Phe Glu Leu Ala Val Lys Phe Glu Thr Leu Val Ser Leu
                325                 330                 335

Arg Phe Pro Leu Asp Gln His Pro Arg Arg Ala Gln Pro Gly Ser Arg
                340                 345                 350

Ser Gln Pro Ser Ser Leu Ala Ser Ser Arg Pro Leu Ala Glu Met Pro
                355                 360                 365

Gln Pro Tyr Gly Ser Leu Pro Pro Val Ala Phe Glu Lys Met Leu
370                 375                 380

Gly Asp Ala Ile Ser Thr Thr Lys Ala Asn Ala Asp Ile Leu Pro Val
385                 390                 395                 400

Ser Thr Leu Leu Ser Val Ala His Ala Ala Arg Leu Gly Val Gln
                405                 410                 415

Val Phe Ser Phe Ala Ser Ala Leu Arg Arg Ala Leu Val Leu Leu
                420                 425                 430

Pro Glu Ile Lys Asn Pro Ala Ala Phe Ile Arg Leu Leu Gln Asp Leu
    435                 440                 445

Glu Lys Leu Gly Gly Leu Gly Asp Arg His Phe Val Phe Phe Arg Glu
    450                 455                 460

Lys Val Lys Glu Thr Leu Gln Ser Ala Ser Ser Arg Cys Ser Leu Phe
465                 470                 475                 480

Gly Thr Ala Leu Val Val His Leu Leu Ala Arg His Arg Leu Arg Asp
                485                 490                 495

Glu Glu Leu Leu Thr Leu Ala Tyr Arg Arg Phe Ser Arg Asn Arg Tyr
                500                 505                 510

Thr Leu Ala Ala Ala Val Arg Gln Thr Pro Ser Leu Leu Ala Ala Leu
                515                 520                 525

Pro Leu Ala Leu Ser Arg Leu Glu Val Pro Thr Leu Ala Ala Ala Val
530                 535                 540

Leu Asp Ser Leu Leu Ser Asp Gln Ala Pro Ala Ala Val Ser Gln Leu
545                 550                 555                 560

Ser Ile His Glu Leu Ser Asn Leu Ala Tyr Ala Ile Ala Cys Val Ser
                565                 570                 575

Thr Asn Ser Gln Val Thr Val Asp Thr His Pro Ser Ser Ala Asp Ser
                580                 585                 590

Gly Ser Cys His Glu Gln Arg Pro Glu Arg Phe Glu Val Gly Ser Ser
                595                 600                 605
```

Glu Lys Glu Cys Gln Ser Gly Met Lys Met Gln Leu His Pro Glu His
610             615                 620

Arg Ser Val Arg Glu Gln Tyr Asn Ala Ser Glu Val Asp Pro Gly Glu
625             630                 635                 640

Asn Ser Ala Thr Gly Gly Val Gly Asp Pro Phe Leu Gly Asn Lys
            645                 650                 655

Arg Glu Asn Asn Thr Ser Phe Lys Val Leu Glu Ser Arg Ser Val Cys
            660                 665                 670

Thr Pro Glu Glu Leu Arg Arg Ser Thr Leu Leu Thr Thr Ile Leu
            675                 680                 685

Arg Thr Leu Ser Arg Ser Ser Leu Arg Arg His Pro Leu Asn Ser Pro
690             695                 700

Phe Glu Arg Ala Trp Arg Gln Leu Lys Ile Ile Asp Leu Tyr Leu Gln
705             710                 715                 720

Phe Asn Val Gly Pro Leu Arg Val Asp Asp Glu Ala Leu Gln Phe
            725                 730                 735

Leu Ser Leu Ala Arg Thr Lys Lys Leu Leu Asn Leu Val His Val Ser
            740                 745                 750

Gln Val Gln Lys Arg Val Gly Arg Leu Leu Phe Asp Glu Gly Leu Met
            755                 760                 765

Ser Glu Ile Asp Val Glu Tyr Pro Leu Gly Pro Tyr Val Leu Asp Phe
770             775                 780

Ala Ile Pro Ser Arg Lys Leu Val Val Glu Val Asp Gly Glu Ala His
785             790                 795                 800

Phe Phe Phe Gly Thr Thr Val Pro Thr Ala Gln Thr Arg Met Lys Arg
            805                 810                 815

Glu Leu Leu Ala Ala Met Gly Trp Arg Val Val Val Pro Gln Glu
            820                 825                 830

Leu Trp Arg Asn Lys Arg Lys Gly Lys Ile Lys Glu Phe Val Ala Arg
835             840                 845

Lys Val Arg Glu Gly Leu Glu Ile Asp Asn Ser Asp Arg
850             855                 860

<210> SEQ ID NO 5
<211> LENGTH: 21
<212> TYPE: DNA
<213> ORGANISM: Artificial Sequence
<220> FEATURE:
<223> OTHER INFORMATION: forward primer

<400> SEQUENCE: 5
tcacactgtg cccatctacg a                                          21

<210> SEQ ID NO 6
<211> LENGTH: 22
<212> TYPE: DNA
<213> ORGANISM: Artificial Sequence
<220> FEATURE:
<223> OTHER INFORMATION: reverse primer

<400> SEQUENCE: 6
gtggtgaagc cgtatcctct ct                                         22

<210> SEQ ID NO 7
<211> LENGTH: 20
<212> TYPE: DNA
<213> ORGANISM: Artificial Sequence
<220> FEATURE:
<223> OTHER INFORMATION: forward primer

```
<400> SEQUENCE: 7
tccaacatcc cgacctgatc                                                          20

<210> SEQ ID NO 8
<211> LENGTH: 21
<212> TYPE: DNA
<213> ORGANISM: Artificial Sequence
<220> FEATURE:
<223> OTHER INFORMATION: reverse primer

<400> SEQUENCE: 8
gcttcgacct tcgcattctt c                                                        21
```

US 10,060,922 B2

IN VIVO INDUCED TOXOPLASMA GONDII PROTEIN FOR APPLICATION IN DIAGNOSIS, VACCINE AND THERAPY

This application is a 35 U.S.C. § 371 filing of International Application No. PCT/IB2015/057522, filed on Oct. 1, 2015, which claims priority to Malaysia Patent Application No. PI2014002940, filed on Oct. 16, 2014, the contents of each of which are incorporated herein by reference in their entirety.

SEQUENCE LISTING

This application contains a Sequence Listing in computer readable format. The name of the text file containing the Sequence Listing is 590221_MCT-020US_Sequence_Listing.txt. The text file is about 13,931 bytes, and was created on Oct. 23, 2017. The information in the computer readable format of the Sequence Listing is incorporated herein by reference in its entirety.

FIELD OF THE INVENTION

The present invention relates to methods of screening biological samples for the presence of *Toxoplasma gondii*. More particularly, the present invention relates to a sensitive and specific screening test for the presence of anti-*T. gondii* IgM in subjects using particular in vivo-induced *T. gondii* antigens which have diagnostic efficacy. The invention further relates to the use of an in vivo-induced antigen in a vaccine against *Toxoplasma* infection.

BACKGROUND

Toxoplasmosis is a widespread infectious disease in man and animals, with variable prevalence in different countries, depending on socio-economic habits and climate. The seroprevalence of *Toxoplasma gondii* (*T. gondii*) infection is up to 95% in some populations especially in areas with hot, humid, climates and lower altitudes; and lower in colder areas. This is because moist, warm soil is favorable for *T. gondii* oocysts which are able to survive for about 1 year (Remington et al., Toxoplasmosis. In: Infectious diseases of the fetus and newborn infant. 7th edition. Edited by Remington J S, Klein J O, Wilson C B, Nizet V, Maldonado Y A. Pennsylvania: Elsevier Saunders; 2011: 915-1041). It has been reported that *T. gondii* seroprevalence in women at child-bearing age (1990-2000) was 51-72% in several Latin-American countries, 58% in Central European countries, and 54-77% in West African countries. Low seroprevalences of 4 to 39% were reported in southwest Asia, Korea and China as well as in cold and arid climate areas such as Scandinavian countries (11-28%). Meanwhile in the USA, a seroprevalence of 9.0% was recorded for 12-49 year old people during 1999-2004 (Nutter et al., *JAMA* 2004; 229: 1394-1398). In Malaysia seroprevalence among 200 pregnant women at University Malaya Medical Centre in 2003 was reported to be ~49%, and the highest prevalence was in Malays, followed by Indians (Nissapatorn & Abdullah, Southeast Asian J Trop Med Public Health. 2004 March; 35(1): 24-30).

*Toxoplasma* can be transmitted to humans by three main routes i.e. (i) ingestion of oocysts released by infected cats in their feces. Humans are exposed to oocysts from cat litter or from soil as a result of activities like gardening or eating unwashed fruits or vegetables; (ii) ingestion of raw or inadequately cooked infected meat; and (iii) a newly infected pregnant woman passing the infection to her unborn fetus, causing congenital toxoplasmosis. In addition, immunocompromised patients such as those with AIDS and those undergoing organ transplantation are at risk of reactivated or primary infection.

Congenital toxoplasmosis is one of the most important manifestations of the infection. Acute infections in seronegative pregnant women can be transmitted to the fetus and cause severe illnesses e.g. abortion, intracranial lesions, mental retardation, retinochoroiditis, blindness, and epilepsy. An estimated 400-4,000 cases of congenital toxoplasmosis occur each year in the United States (Lopez et al., MMWR Recomm Rep. 2000 Mar. 31; 49(RR-2): 59-68); and 9% of those children have significant visual impairment (Tan et al., Am J Ophthalmol 2007; 144: 48-653). The global annual incidence of congenital toxoplasmosis is estimated to be 190,100 cases, and it is equivalent to 1.20 million DALYs, with high burdens reported in South America, some Middle Eastern countries and low-income countries (Torgerson & Mastroiacova, Bull World Health Organ. 2013 Jul. 1; 91(7): 501-8). It was estimated that the expense of a patient with severe congenital toxoplasmosis was about USD 1 million (Remington et al., Toxoplasmosis. In: Infectious diseases of the fetus and newborn infant. 7th edition. Edited by Remington J S, Klein J O, Wilson C B, Nizet V, Maldonado Y A. Pennsylvania: Elsevier Saunders; 2011: 915-1041).

A panel of tests is usually performed on serum samples of persons with suspicion of infection. This includes testing for IgM and IgG and performing IgG avidity assays. Usually, specific IgM appears 1 week after infection and IgG appears 1 to 3 weeks later (Jenum et al., *J Clin Microbiol* 1998; October; 36(10): 2907-13). Thus, anti-*T. gondii* IgM is usually the first assay performed; or both IgM and IgG assays are performed at the same time. If both are positive, then IgG avidity test is often performed; low IgG avidity indicates that the infection may be acute whereas high IgG avidity confirms it is a chronic infection.

The availability of a highly sensitive IgM test is important. Currently, there is no reference *Toxoplasma* IgM test. One of the more sensitive tests for IgM detection is ISAGA (immunosorbent agglutination assay), a micro agglutination plate assay produced in France (BioMereieux); however it is not frequently used in developing countries due to its high cost. The most common serological test format in routine diagnosis of toxoplasmosis is ELISA. Major diagnostic laboratories use ELISA kits adapted for expensive fully automated systems such as VIDAS® (BioMerieux, France), ARCHITECT™ (Abbot, USA) and LIAISON® (DiaSorin, USA). The result using these advanced systems is usually quite reliable. Nevertheless, even the detection of IgM in newborns using these advanced systems is still a challenge as evidenced in a recent report that showed only 3 of 10 cases of newborns with confirmed congenital toxoplasmosis were detected using LIAISON® and VIDAS® (Murat et al., *Expert Rev Anti Infect Ther* 2013 September; 11(9): 943-56). Thus there is still a need for development of a highly sensitive and highly specific test for detection of specific IgM to indicate *T. gondii* infection using well-defined antigens.

The host-pathogen interaction during infectious disease is complex, multifaceted and dynamic. All regulated virulence factors of a pathogen cannot be determined only by using in vitro methods, since it is impossible to reproduce all the various environmental stimuli that occur at the site of the actual infection. Genes induced only or at greater level during in vivo growth (as compared to in-vitro growth) may be virulence determinants and are thus important in the natural pathogenesis process (Valdivia and Falkow, *Science*, 1997; 277: 2007-2011 Angelichio and Camilli, *Infection and Immunity* 2002; 70: 6518-6523). These in vivo-induced proteins have good potential as diagnostic markers, vaccine candidates, therapeutic targets and in further understanding of the pathogenesis of the pathogen (Handfield et al., *Trends Microbiol* 2000; 8: 336-39; John et al., *Infection and Immunity* 2005; 73: 2665-79; Hongwei et al., 2009; Lowry et al., *Plos One,* 2011; 6 (3): e17425).

To identify the in vivo induced proteins, several techniques have been used such as signature-tagged mutagenesis (STM) (Hensel et al., *Science,* 1995; 269: 400-403), in vivo expression technology (IVET) (Angelichio and Camilli, *Infection and Immunity* 2002; 70: 6518-6523), differential fluorescence induction (DFI) (Valdivia and Falkow, *Science,* 1997; 277: 2007-2011) and transcriptional and proteomic profiling (Ramachandran et al., *Science* 2004; 305: 86-90). Although these techniques have contributed significantly to expand the understanding of pathogen pathogenesis, they have some important limitations. Most notably they require an animal model to monitor the pathogen mechanism which may not adequately mimic events in an actual site of infection within the natural human host.

In vivo-Induced Antigen Technology (IVIAT), a modification of previously described immunologic screening techniques of protein expression libraries, has been introduced to identify antigens expressed specifically in vivo during natural human infection (Handfield et al., *Trends Microbiol* 2000; 8: 336-39). IVIAT has been used with the same goals as STM, IVET and DR yet does not need the use of animal models. IVIAT is preferred to those other techniques since it directly examines human immune responses by utilizing sera from patients infected with a pathogen of interest, thus reducing false-positive results caused by the differences between proteins expressed during actual human infection and in-vitro conditions (Handfield et al, *Trends Microbiol* 2000; 8: 336-39). So far, IVIAT has successfully been applied to the study of over 30 different prokaryotic and eukaryotic organisms. We have previously used IVIAT to identify a number of in vivo-induced antigens in chronic and acute human toxoplasmosis (Amerizadeh et al., *Microb Pathog.* 2013a; 54: 60-66; Amerizadeh et al., *BMC Infectious Disease* 2013b; 13: 287-299). Although three antigens were induced 54-330 fold in vivo over in vitro levels, the sensitivity and specificity for detecting *T. gondii*-IgM was only 90% and 40-70%, respectively.

There is a need to identify *T. gondii* antigens that are highly induced in vivo compared to in vitro and which have high sensitivity and specificity for detecting *T. gondii*-IgM, as they would not only be useful for diagnosing toxoplasmosis but would also be potential vaccine candidates.

There is currently no vaccine for human *Toxoplasma* infection. Vaccines for animal infection are available but can be improved. There is also a need to improve treatment for toxoplasmosis, especially for congenital infection.

SUMMARY OF THE INVENTION

The *T. gondii* RAP domain-containing protein identified in this study is significantly induced in vivo in subjects with toxoplasmosis and has high specificity and sensitivity for *T. gondii*-specific IgM. Therefore, the protein and/or antibodies produced against the protein are highly suitable as indicators of infection and/or as a therapeutic target.

Accordingly, in a first aspect, the present invention provides the use of an isolated or recombinant *T. gondii* RAP domain-containing protein, or a fragment or variant thereof, to detect *Toxoplasma* in a biological sample isolated from a subject.

In a preferred embodiment of the invention the RAP domain-containing protein comprises the amino acid sequence shown in SEQ ID NO: 2 or SEQ ID NO: 4 or a fragment or variant thereof.

In another preferred embodiment of the invention the RAP domain-containing protein or fragment or variant thereof is encoded by an isolated or recombinant nucleic acid molecule comprising the nucleic acid sequence shown in SEQ ID NO: 1 or SEQ ID NO: 3 or a fragment thereof.

Preferably, toxoplasmosis is indicated by specific and selective binding of the RAP domain-containing protein to *T. gondii*-specific IgM present in a biological sample isolated from the subject.

According to another aspect of the invention, there is provided a method of detecting *T. gondii* in a biological sample, comprising the steps of:

a) providing at least one biological sample;

b) contacting the at least one biological sample with an antigen, wherein the antigen is an isolated or recombinant *T. gondii* RAP domain-containing protein or a fragment thereof; and c) detecting specific and selective antigen-antibody binding, wherein the binding indicates the presence of *T. gondii*-specific antibodies present in the test sample.

In a preferred embodiment of the method of the invention, the antigen-antibody binding is detected using immunoassay.

According to another aspect of the invention, there is provided a method of detecting *T. gondii* in a biological sample, comprising the steps of:

a) providing at least one biological sample;

b) detecting the presence of *T. gondii* RAP domain-containing protein, or nucleic acid molecule encoding same, in the biological sample, wherein the detection of the RAP domain-containing protein or nucleic acid molecule in the biological sample constitutes detection of *T. gondii.*

In a preferred embodiment of the method of the invention, the RAP domain-containing protein comprises the amino acid sequence shown in SEQ ID NO: 2 or SEQ ID NO: 4 and the nucleic acid comprises the nucleic acid sequence shown in SEQ ID NO: 1 or SEQ ID NO: 3.

In another preferred embodiment of the method of the invention, the RAP domain-containing protein is detected with an antibody that specifically and selectively binds the protein, and the nucleic acid is detected using nucleic acid amplification.

In another preferred embodiment of the method of the invention, the RAP domain-containing protein is detected using immunoassay.

According to another aspect of the invention, there is provided a method of detecting whether a subject has toxoplasmosis, comprising the steps;

a) contacting a test sample from the subject with an antigen, wherein the antigen is an isolated or recombinant *T. gondii* RAP domain-containing protein or a fragment thereof, and detecting specific and selective antibody-antigen binding, wherein the binding indicates the presence of toxoplasmosis in the subject; or b) detecting the presence of *T. gondii* RAP domain-containing protein, or nucleic acid molecule encoding same, in a test sample from the subject, wherein the detection of the RAP domain-containing protein or nucleic acid molecule in the test sample indicates the presence of toxoplasmosis.

In another preferred embodiment of the method of the invention, the RAP domain-containing protein or fragment or variant thereof is encoded by an isolated or recombinant nucleic acid molecule comprising the nucleic acid sequence shown in SEQ ID NO: 1 or SEQ ID NO: 3 or a fragment thereof.

In another preferred embodiment of the method of the invention, the *T. gondii* specific antibodies are IgM antibodies.

According to another aspect of the invention, there is provided a vaccine comprising at least one *T. gondii* RAP domain-containing protein or antigenic fragment or variant thereof.

According to another aspect of the invention, there is provided a method of treatment or prophylaxis of toxoplasmosis, comprising administering to a subject an efficacious amount of a vaccine as defined above.

According to another aspect of the invention, there is provided a use of at least one *T. gondii* RAP domain-containing protein or antigenic fragment or variant thereof for the preparation of a vaccine for the prophylaxis or treatment of toxoplasmosis.

According to another aspect of the invention, there is provided an expression construct comprising a nucleic acid comprising the sequence shown in SEQ ID NO: 1 or SEQ ID NO: 3 or a fragment thereof.

In a preferred embodiment the nucleic acid comprises the sequence shown in SEQ ID NO: 1 or antigen encoding fragment thereof.

According to another aspect of the invention, there is provided a kit for screening a biological sample for the presence of *T. gondii*-specific antibody and/or *T. gondii* antigen, comprising:

a) an isolated or recombinant RAP domain-containing protein, or a fragment thereof as defined in claim 1 or 2, capable of binding to *T. gondii*-specific antibody present in the biological sample; and/or b) an isolated or recombinant RAP domain-containing protein-specific antibody as defined in claim 10, capable of binding to *T. gondii* RAP domain-containing protein present in the biological sample; and/or c) oligonucleotide primers capable of binding to and amplifying at least a portion of a *T. gondii* RAP domain-containing protein encoding nucleic acid or cDNA derived therefrom present in the biological sample.

In a preferred embodiment, the kit further comprises immunoassay reagents when a) or b) are present, and further comprises nucleic acid amplification reagents when c) is present.

In a preferred embodiment, the oligonucleotide primers are directed to a portion of the nucleotide sequence shown in SEQ ID NO: 3.

In a preferred embodiment, the kit according to c) further comprises oligonucleotide probes capable of binding to the amplified portion of the *T. gondii* RAP domain-containing protein encoding nucleotide sequence.

BRIEF DESCRIPTION OF THE FIGURES

FIG. 2: Nucleotide sequence of phage clone AM15 of in vivo-induced *T. gondii* RAP (RNA Associated Protein) domain-containing protein represented by SEQ ID NO: 1 which encodes an antigenic fragment containing the epitope that binds to *T. gondii*-specific IgM.

FIG. 3: Amino acid sequence encoded by phage clone AM15 of in vivo-induced *T. gondii* RAP (RNA Associated Protein) domain-containing protein, designated rTgRA15 and represented by SEQ ID NO: 2

FIG. 4: TGGT1_269830 or TGME49_269830 or TGVEG_017050: DNA sequence encoding full length RAP domain-containing protein represented by SEQ ID NO: 3. The AM15 clone sequence is highlighted and underlined.

FIG. 5: Predicted protein sequence of TGME_269830 RAP domain-containing protein: SEQ ID NO: 4, with rTgRA15 antigen sequence underlined.

DETAILED DESCRIPTION

Definitions

Figure 1:
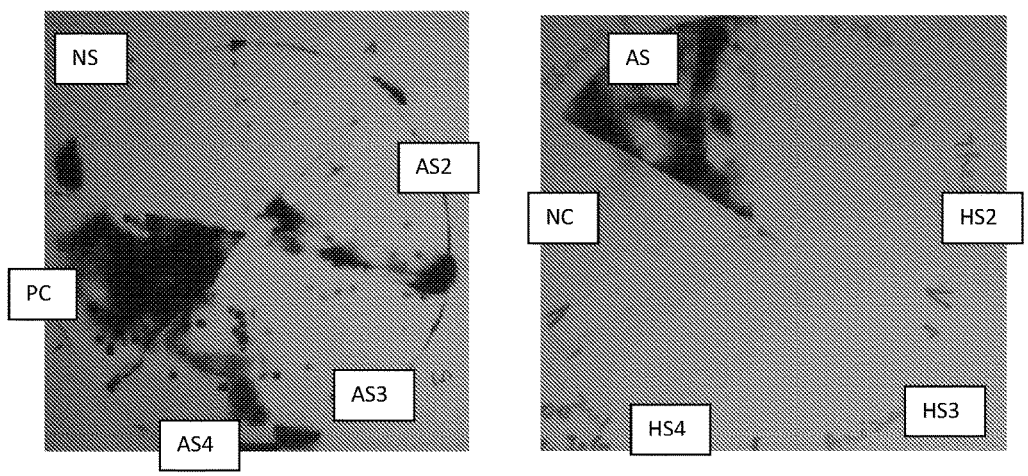
FIG. 1: Representative results of sensitivity and specificity evaluation of phage clone AM15. HS: serum from a healthy person; AS: serum from person with acute toxoplasmosis; PC: positive control serum; NC: negative control serum.

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. The term "RAP domain-containing protein sequence", as used herein, refers to an antigenic polypeptide used to identify and or generate RAP domain-containing protein-specific antibodies.

In this context, "fragments" refers to a RAP domain-containing protein according to the invention which has been reduced in length by one or more amino acids and which retains antigenic activity of RAP domain-containing protein sufficient to raise and or detect antibodies specific to RAP domain-containing protein. For example, the rTgRA15 antigen described in the present application is produced from the AM15 DNA clone of SEQ ID NO: 1 and has the amino acid sequence set forth in SEQ ID NO: 2, and may be considered a fragment of the full length RAP domain-containing protein of SEQ ID NO: 4 (as underlined in FIG. 5). It would be understood that the rTgRA15 antigen polypeptide could be further reduced in length (i.e. fragmented) and retain a *T. gondii* RAP domain-containing protein epitope that binds to serum IgM from subjects with toxoplasmosis.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody. In the context of the invention, specificity refers to the lack of reactivity of the RAP domain-containing protein with serum from healthy individuals or from patients with other infections. Thus if 9 serum samples are not reactive out of 10 healthy sera, the specificity of the antigen in the detection of anti-*T. gondii* antibodies is 90%.

As used herein, the term "sensitive binding" or "sensitivity" refers to the number of serum samples from *T. gondii* infected individuals which are reactive with the RAP domain-containing protein. Thus if 8 serum samples are reactive out of 10 infected sera, the sensitivity of the antigen in the detection of anti-*T. gondii* antibodies is 80%.

An antibody is any immunoglobulin, including antibodies and fragments thereof that bind to a specific epitope. The antibody according to the invention may be prepared against a polypeptide having the amino acid sequence of at least one of SEQ ID NOS: 2 or 4 or a fragment thereof. Such antibodies include, but are not limited to isolated and/or recombinant polyclonal, monoclonal, chimeric, humanised, single chain, Fab, Fab', F(ab)' fragments and/or F(v) portions of the whole antibody.

The term 'variant', as used in the context of the present invention is intended to describe variations to the amino acid sequence of the RAP domain-containing protein that do not remove the antigenicity of the polypeptide in terms of eliciting antibodies which bind to the RAP domain-containing protein. Variants include conservative amino acid substitutions, and additions or deletions of amino acids that do not affect antigenicity.

A "conservative amino acid substitution" as used herein is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, one or more amino acid residues in a RAP domain-containing protein comprising, essentially consisting of, or consisting of the amino acid sequence encoded by the nucleic acid sequence SEQ ID NO: 1, or a fragment thereof, may be replaced with one or more other amino acid residues from the same side chain family without significantly reducing the antigenicity of the polypeptide or deviating significantly from the scope of the present invention.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay. As used herein, the term "oligonucleotide" is substantially equivalent to the terms "amplimers," "primers," "oligomers," and "probes," as these terms are commonly defined in the art.

The term "antisense," as used herein, refers to any composition containing a nucleic acid sequence which is complementary to a specific polynucleotide sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "small interfering RNA" (siRNA), as used herein, refers to small pieces of double-stranded (ds) RNA, usually about 21 nucleotides long, with 3' overhangs (2 nucleotides) at each end that can be used to interfere with the translation of proteins by binding to and promoting the degradation of messenger RNA (mRNA) at specific sequences. In doing so, they prevent the production of specific proteins based on the nucleotide sequences of their corresponding mRNA. Suitable siRNA's for use according to the invention can be based on the nucleic acid which encodes the *T. gondii* RAP domain-containing protein. More specifically, suitable siRNA's may be based on the nucleic acid comprising SEQ ID NO: 1 or SEQ ID NO: 3.

The term "treatment", as used in the context of the invention refers to prophylactic, ameliorating, therapeutic or curative treatment.

The term "comprising" as used in the context of the invention refers to where the various components, ingredients, or steps, can be conjointly employed in practicing the present invention. Accordingly, the term "comprising" encompasses the more restrictive terms "consisting essentially of" and "consisting of". With the term "consisting essentially of" it is understood that the epitope/antigen of the present invention "substantially" comprises the indicated sequence as "essential" element. Additional sequences may be included at the 5' end and/or at the 3' end. Accordingly, a polypeptide "consisting essentially of" sequence X will be novel in view of a known polypeptide accidentally comprising the sequence X. With the term "consisting of" it is understood that the polypeptide, polynucleotide and/or antigen according to the invention corresponds to at least one of the indicated sequence (for example a specific sequence indicated with a SEQ ID Number or a homologous sequence or fragment thereof).

A person skilled in the art will appreciate that the present invention may be practiced without undue experimentation according to the method given herein. The methods, techniques and chemicals are as described in the references given or from protocols in standard biotechnology and molecular biology text books such as Sambrook and Russell, Molecular Cloning: A Laboratory Manual, Cold Springs Harbor Laboratory, New York (2001).

In a first aspect, the present invention provides the use of an isolated or recombinant *T. gondii* RAP domain-containing protein, or a fragment or variant thereof, to detect *Toxoplasma* in a biological sample isolated from a subject. The terms 'fragment' and 'variant' have been defined above.

The native form of this protein is significantly induced when *T. gondii* is present in-vivo in a host (human or animal) compared to when it is present in-vitro (cell culture).

A preferred embodiment according to any aspect of the invention relates to a RAP domain-containing protein comprising the amino acid sequence shown in SEQ ID NO: 2 or SEQ ID NO: 4 or a fragment or variant thereof. The polypeptide of SEQ ID NO: 2, which is a fragment of the protein of SEQ ID NO: 4, contains an epitope that is recognized by IgM present in subjects with toxoplasmosis.

In another preferred embodiment of the invention the RAP domain-containing protein or fragment or variant thereof is encoded by an isolated or recombinant nucleic acid molecule comprising the nucleic acid sequence shown in SEQ ID NO: 1 or SEQ ID NO: 3 or a fragment or variant thereof. The protein of SEQ ID NO: 2, encoded by an expression construct containing the nucleic acid of SEQ ID NO: 1, was found to possess highly specific and selective binding to antibodies from subjects with toxoplasmosis.

Preferably, toxoplasmosis is indicated by specific and selective binding of the RAP domain-containing protein or fragment thereof to *T. gondii*-specific IgM present in a biological sample isolated from the subject. The biological sample may be from any body fluid which may contain antibodies to *T. gondii*. Such body fluids may include blood, serum, eye fluid, cerebrospinal fluid or amniotic fluid. Preferably, the sample is a blood sample, more preferably a serum sample.

The indication may be acute toxoplasmosis in the subject.

The binding of the RAP domain-containing protein or fragment thereof to antibodies may be detected using any suitable immunoassay technique. For example, the detection assay may be performed by methods such as ELISA, western blot, flow-through assay or lateral flow assay (LFA) using various labeling techniques such as enzyme amplification, radioactivity or fluorescence. An advantage of using LFA is that it is cheap and easy to use and provides results in 15-20 minutes (such as the dipstick dot test exemplified herein).

According to another aspect of the invention, there is provided a method of detecting *T. gondii* in a biological sample, comprising the steps of:
a) providing at least one biological sample;
b) contacting the at least one biological sample with an antigen, wherein the antigen is an isolated or recombinant *T. gondii* RAP domain-containing protein or a fragment thereof; and
c) detecting specific and selective antigen-antibody binding, wherein the binding indicates the presence of *T. gondii*-specific antibodies present in the test sample.

According to another aspect of the invention, there is provided a method of detecting *T. gondii* in a biological sample, comprising the steps of:
a) providing at least one biological sample;
b) detecting the presence of *T. gondii* RAP domain-containing protein, or nucleic acid molecule encoding same, in the biological sample, wherein the detection of the RAP domain-containing protein or nucleic acid molecule in the biological sample constitutes detection of *T. gondii*.

In a preferred embodiment of the method of the invention, the RAP domain-containing protein comprises the amino acid sequence shown in SEQ ID NO: 4 and the nucleic acid comprises the nucleic acid sequence shown in SEQ ID NO: 3. It would be understood that any region of the nucleic acid could be the detection target.

In another preferred embodiment of the method of the invention, the RAP domain-containing protein is detected with an isolated or recombinant antibody that specifically and selectively binds the protein, and the nucleic acid is detected using real time PCR or any other formats of nucleic acid amplification and detection. Labeled or unlabeled oligonucleotide primers and/or probes could be directed to any suitable region of the nucleic acid molecule.

According to another aspect of the invention, there is provided a method of detecting whether a subject has toxoplasmosis, comprising the steps;
a) contacting a biological sample from the subject with an antigen, wherein the antigen
is an isolated or recombinant *T. gondii* RAP domain-containing protein or a fragment thereof, and detecting specific and selective antibody-antigen binding, wherein the binding indicates the presence of toxoplasmosis in the subject; or b) detecting the presence of *T. gondii* RAP domain-containing protein, or nucleic acid molecule encoding same, in a biological sample from the subject, wherein the detection of the RAP domain-containing protein or nucleic acid molecule in the test sample indicates the presence of toxoplasmosis.

It would be understood that fragments or variants of the protein could be generated using recombinant and/or PCR technology that could still function as an antigen to bind to *T. gondii*-specific antibodies in a test sample.

In another preferred embodiment of the method of the invention, the *T. gondii*-specific antibodies in the biological sample from a subject with toxoplasmosis are RAP domain-containing protein-specific IgM antibodies.

The methods of the invention may detect or indicate toxoplasmosis in a subject.

The subject may be an animal or human. Preferably the subject is a human. More preferably the human is a neonate, baby, pregnant woman or other individual with acquired toxoplasmosis.

There have been increasing efforts in the development of treatment for toxoplasmosis. An example is the use of antigens obtained from tachyzoites in combination with Alum as shown by Costa-Silva et al. (*Exp Parasitol*, 2008; 120(3): 227-34). This crude method produced an increased antibody level with reduced parasitemia and delayed mortality.

In an attempt to increase specificity, certain biomarkers have been utilized as vaccine candidates. Examples include the use of both DNA and recombinant surface antigens such as recombinant surface antigen 1 (SAG1) protein [Letscher-Bru, V., et al., *Infect Immun* 2003; 71(11): 6615-9] or a plasmid incorporating SAG-1 [Chen, G., et al., *Chin Med J* (Engl), 2002; 115(10): 1448-52], secreted granule antigen 1 to 7 (GRA1-GRA7) DNA vaccine [Jongert, E., et al., *Vaccine* 2008; 26(8): 1025-31] and an aspartic protease 1 (TgAsp1) DNA vaccine [Zhao, G., et al., *Parasit Vectors* 2013; 6: 175]. All of these publications which are incorporated herein by reference teach suitable methods of generating DNA expression constructs comprising nucleic acids encoding immunogenic target peptides and use as vaccines with efficacies in terms of increased survivability, increased TH1/TH2 responses and resistance to challenge with cysts. The *T. gondii* RAP domain-containing protein or nucleic acid, with its high in vivo induction, is suitable as an immunotherapy candidate.

According to another aspect of the invention, there is provided a vaccine comprising at least one *T. gondii* RAP domain-containing protein or antigenic fragment thereof. DNA which encodes *T. gondii* RAP domain-containing protein or antigenic fragment thereof when included in an expression vector may also be suitable in a vaccine to generate an immune response.

In a preferred embodiment of the vaccine, the RAP domain-containing protein comprises the amino acid sequence shown in SEQ ID NO: 2 or SEQ ID NO: 4 or an antigenic fragment or variant thereof.

In another preferred embodiment of the vaccine, the RAP domain-containing protein is encoded by a nucleic acid comprising the sequence shown in SEQ ID NO: 1 or SEQ ID NO: 3 or a fragment thereof.

The *T. gondii* RAP domain-containing protein or antigenic fragments of the invention may be produced for immunization purposes synthetically or via expression constructs which encode them. An example of a suitable expression vector is the bacterial plasmid pET28 (Invitrogen, USA) used in the Examples.

Modifications and changes may be made in the structure of the DNA segments which encode the polypeptides and still obtain a functional molecule that encodes a peptide that can elicit an immune response against *T. gondii* RAP domain-containing protein. The nucleic acid molecules according to the invention can contain naturally occurring sequences, or sequences that differ from those that occur naturally, but, due to the degeneracy of the genetic code, encode the same polypeptide (for example, the peptide with SEQ ID NO: 4, or rTgRA15 of SEQ ID NO: 2 encoded by the nucleic acid SEQ ID NO: 1).

The nucleic acid molecules according to the invention may have sequence changes that cause a conservative amino acid substitution that does not significantly reduce the *T. gondii* RAP domain-containing protein antigenicity. The isolated nucleic acid molecules according to the invention encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location).

The DNA may be expressed in a suitable host to produce a polypeptide comprising the *T. gondii* RAP domain-containing protein or antigenic fragment thereof according to any aspect of the invention. Thus, the DNA encoding the peptide of the invention may be used in accordance with known techniques, to construct an expression vector, which is then used to transform an appropriate host cell for the expression and production of the peptide according to the invention.

In yet another aspect of the present invention there is provided at least one plasmid or vector (expression construct) comprising the nucleic acid molecule according to any aspect of the present invention. Preferably, the expression construct comprises the nucleic acid comprising the sequence shown in SEQ ID NO: 1 or SEQ ID NO: 3 or a fragment thereof which encodes an antigenic peptide.

According to another aspect of the invention, there is provided a method of treatment or prophylaxis of toxoplasmosis, comprising administering to a subject an efficacious amount of a vaccine comprising at least one *T. gondii* RAP domain-containing protein, antigenic fragment thereof or expression construct comprising DNA encoding same, or at least one siRNA specific for a nucleic acid which encodes the *T. gondii* RAP domain-containing protein.

In another preferred embodiment of the method, the siRNA is specific for a RAP domain-containing protein encoding nucleic acid comprising the sequence shown in SEQ ID NO: 1, SEQ ID NO: 3 or a fragment thereof.

According to another aspect of the invention, there is provided the use of at least one *T. gondii* RAP domain-containing protein or antigenic fragment or variant thereof, or expression construct comprising DNA encoding same, for the preparation of a vaccine for the prophylaxis or treatment of toxoplasmosis.

According to another aspect of the invention, there is provided a kit for screening a biological sample for the presence of *T. gondii*-specific antibody and/or *T. gondii* antigen, comprising:

a) an isolated or recombinant RAP domain-containing protein, or a fragment thereof as defined herein, capable of binding to *T. gondii*-specific antibody present in the biological sample; and/or b) an isolated or recombinant RAP domain-containing protein-specific antibody as defined herein, capable of binding to *T. gondii* RAP domain-containing protein present in the biological sample; and/or c) isolated oligonucleotide primers capable of binding to and amplifying at least a portion of a *T. gondii* RAP domain-containing protein encoding nucleic acid or cDNA derived therefrom present in the biological sample.

In a preferred embodiment, the kit further comprises immunoassay reagents when a) or b) are present, and further comprises nucleic acid amplification reagents when c) is present.

In a preferred embodiment, the oligonucleotide primers are directed to a portion of the nucleotide sequence shown in SEQ ID NO: 3.

In a preferred embodiment, the kit according to c) further comprises oligonucleotide probes capable of binding to the amplified portion of the *T. gondii* RAP domain-containing protein encoding nucleotide sequence.

The kit for immunoassay may also contain suitable solid supports for western blot, dot blot, ELISA, flow-through assay, LFA or any other immunoassay platform.

Having now generally described the invention, the same will be more readily understood through reference to the following examples which are provided by way of illustration, and are not intended to be limiting of the present invention.

EXAMPLES

Parasite Strain and Growth Conditions

In-vitro culture of *T. gondii* RH strain in Vero cells was performed under conditions previously optimized in our laboratory. Briefly, VERO cells were washed four times at 85% confluence with phosphate buffered saline (PBS), followed by addition of DMEM medium (Gibco BRL, USA) containing 100 µg/ml streptomycin and 100 IU/ml penicillin (Gibco BRL, USA) with 10% (v/v) fetal bovine serum (Invitrogen, USA). Subsequently the cells were seeded with $1 \times 10^7$ *T. gondii* tachyzoites harvested from infected mice. After 3-4 days the maximum release of tachyzoites was observed and the culture containing parasites was centrifuged and the pelleted tachyzoites were kept at −80° C.

To produce in-vivo grown tachyzoites, Swiss albino mice were intra-peritoneally infected with $1 \times 10^3$ tachyzoites of *T. gondii* RH strain. After three to four days post-infection, the peritoneal cavity fluid was aseptically harvested with 5 ml of RPMI-1640 medium containing penicillin streptomycin (RPMI-PS), pH 7.2 (Gibco®, Life Technologies, USA). The supernatant containing tachyzoites was collected, centrifuged, washed with PBS and pelleted tachyzoites immediately kept at −80° C. for RNA extraction.

Serum Samples

Commercial IgM and IgG, IgG avidity ELISA kits (Euroimmun, Germany and Platelia, BioRad, USA) were used to determine the *Toxoplasma* serology status of the serum samples in this study.

For performing IVIAT, twelve sera samples were obtained from patients with clinical evidence of toxoplasmosis. *Toxoplasma* serology performed on the serum samples showed high IgM antibody levels and low IgG avidity indices. Prior to performing IVIAT, equal volumes of each serum samples were pooled. Out of a total of 12 serum samples, 10 were individually used to determine diagnostic sensitivity of selected clones. In addition, 10 serum samples from individuals with evidence of chronic *Toxoplasma* infection (IgM+, IgG+, high IgG avidity), as well as healthy individuals which were negative for both anti-*Toxoplasma* IgM and IgG antibody were individually tested.

For western blot[#] analysis and evaluation of the dipstick tests[*], five groups of serum samples were used, as follows: IgM+, IgG+, low IgG avidity (n=5[#] or 20[*]); IgM+, IgG+, high IgG avidity (n=10); IgM-IgG+(n=19[#] or 11[*]); IgM−IgG−, healthy people (n=18) and IgM−, IgG− other infections (n=12[#] or 10[*]).

Sera Pre-Adsorption

Sera adsorption was performed according to previously reported protocol with some slight modifications in order to increase efficiency of the process so as to 'completely' remove in-vitro antigens [Amerizadeh et al., 2013a]. Each step was repeated twice and thimerosol (1%) was added in order to prevent contamination. Serum samples used for sensitivity and specificity determination were pre-adsorbed with pellet, heat denatured and non-heat-denatured cell lysates of only *E. coli* XL-Blue MRF'. The efficiency of sera adsorption at each step was checked using indirect enzyme-linked immunosorbent assay (ELISA) according to a previously optimized protocol [Amerizadeh et al., 2013a, incorporated herein by reference]. The final adsorbed sera sample was centrifuged and kept at −80° C.

*T. gondii* Expression Library

Custom-made *T. gondii* cDNA expression library was constructed in Lambda ZAP® II system (Strategene, USA) using mRNA from in-vitro grown *T. gondii* pellet. The previously optimized dilution of cDNA library immunoscreening was $10^4$ for primary screening which produces around 500-1000 plaques per plate. For secondary and tertiary screening $10^5$ and $10^6$ dilutions of cDNA library were used respectively.

cDNA Library Immunoscreening to Identify In-Vivo Induced Antigens

For *T. gondii* cDNA library screening a modified version of a previously reported method was used [Hang et al., *Proc Natl Acad Sci USA*. 2003; 100(14) 8508-13]. For primary screening, the $10^3$ dilution of cDNA library was mixed with 600 µl of *E. coli* XL1Blue MRF' cells at optical density of (OD) at 600 nm of 0.5, then plated on LB agar plates 3-4 h in a 42° C. incubator until the plaques became visible. On the next day, the agar plates were overlaid with nitrocellulose filter discs pre-saturated with 10 mM isopropyl-β-D-thiogalactopyranoside (IPTG) and incubated overnight at 28° C. The filters were then removed from the plates, washed (phage plaques side up) with PBS-Tween 20, blocked with 1:5 dilution of Super Block solution (Thermo Scientific, USA) and incubated overnight with adsorbed pooled serum at dilution 1:100. Subsequently after three steps of washing with PBS-Tween 20 the filters were incubated with monoclonal anti-human IgM conjugated with horseradish peroxidase (HRP) (Invitrogen, USA) at 1:2000 dilution for 1 h, washed and then developed using chemiluminescence substrate (Roche Diagnostics, Germany). The phage plaques on the agar plates which corresponded to positive plaque images on the X-ray film were cored out and subjected to secondary and tertiary screenings using the same serum. For secondary and tertiary screenings, higher dilutions were used to produce much lower density plaques (<50 per plate) with many isolated clones. Final positive clones were isolated and placed in 500 µl SM buffer containing 3% chloroform overnight at 4° C. Part of them were used directly for in-vivo excision, while the rest were centrifuged and the supernatant placed in 500 µl SM buffer with 7% DMSO for long-term storage at −80° C.

In-Vivo Excision and Plasmid Purification

In-vivo excision was performed to convert the recombinant phages to recombinant plasmids. The selected phage clone (in 250 µl SM buffer) and 1 µl ExAssist helper phage (>$10^6$ pfu/ml) (Stratagene, USA) was added to 200 µl of *E. coli* XLBlue MRF' cells at OD 1.0 (405 nm). The culture was incubated at 37° C. for 15 min followed by addition of 3 ml of LB broth and incubation in 65° C. for 20 min. After centrifugation 10 µl of supernatant (excised phagemids) was mixed with 200 µl of SOLR cells (Stratagene, USA) at OD 1.0 (405 nm) and plated overnight at 37° C. on LB ampicillin agar plate. Plasmids from each sample were purified using commercial plasmid preparation kit (Promega, USA) and sent for sequencing using M13 forward and reverse primers. The sequences identified by IVIAT in the current study after sequencing were then analyzed using GenBank and ToxoDB databases. ToxoDB, a functional genomic database for *T. gondii* which incorporates sequence and annotation data, is integrated with other genomic-scale data, including community annotation; expressed sequence tags (ESTs) and gene expression data [Khan et al., *Nucleic Acids Res* 2005; 33: 2980-92].

Quantitative Real-Time PCR Analysis

The forward and reverse primers for the sequence were designed using Primer Express 2.0 software (Applied Biosystems, USA). Table 1 shows the primers designed for AM15 clone.

TABLE 1

Primers used for the real-time PCR analysis of target *T. gondii* AM15 clone

| Gene Id/ Accession number | Orientation | Primer sequence |
|---|---|---|
| **β-Actin | Forward | 5'-TCACACTGTGCCCATCTACGA-3' (SEQ ID NO: 5) |
| **β-Actin | Reverse | 5'-TGGTGAAGCCGTATCCTCTCT-3' (SEQ ID NO: 6) |
| 7895000 | Forward | 5'-TCCAACATCCCGACCTGATC-3' (SEQ ID NO: 7) |
| 7895000 | Reverse | 5'-GCTTCGACCTTCGCATTCTTC-3' (SEQ ID NO: 8) |

**β-Actin was used as the housekeeping gene

Pooled in-vitro-grown tachyzoites from 20 culture flasks (75 cm$^2$) (Nunclon, Roskilde, Denmark) and pooled in-vivo-grown tachyzoites from 35 mice were prepared as described above. Total RNA was extracted and purified using RNAeasy mini kit (Qiagen, Germany). The DNase-treated RNA samples were converted to cDNA using High Capacity cDNA Reverse Transcription Kits (Applied Biosystems, USA). Real-time PCR was performed using Quanti FastTect SYBR Green PCR Kit (Qiagen, Germany) in a Rotor Gene 6000 Multiplex System (Corbett Research, Australia). Each of the reaction mix comprised 5 µl of cDNA (200 to 400 ng), 200 pmol of each primer (forward and reverse) and 12.5 µl of 2×SYBR Green mix and sufficient amount of dH$_2$O to bring the volume to 25 µl. The parameters for thermocycler were as follow: 95° C. for 5 min short hot-start, followed by 40 cycles of 95° C. for 10 sec for denaturing and subsequently combine annealing/extension at 60° C. for 30 sec. At the final step of real-time PCR, melting curves with 1° C. temperature increments from 72° C. to 95° C. were incorporated. Data analysis was performed using Rotor Gene 6000 Series Software 1.7. First the expression level was normalized to the reference β-actin gene as housekeeping gene. Next the fold change of in-vivo expression of the gene relative to its in-vitro expression level was calculated using the $2^{-\Delta\Delta Ct}$ method [Livak et al., Methods 2001; 25: 402-8].

Diagnostic Sensitivity and Specificity Determination

To determine the diagnostic sensitivity and specificity of the selected clone, it was plated in petri dishes and immunoscreening was performed as above with the exception that individual serum samples from acutely infected patients were used instead of pooled sera. Each nitrocellulose membrane was divided into six sections i.e. for six different serum samples. Positive and negative controls were included in each experiment. Sensitivity refers to the number of serum samples from acute-infected individuals which were reactive with the protein expressed by a particular clone. Specificity refers to the number of serum samples from healthy individuals or with other infections which were not reactive with the protein expressed by a particular clone.

Preparation and Expression of Recombinant Protein

The IVIAT-identified sequence detected by IgM was custom-cloned into a pET28 expression vector with His-tag fusion (Novagen, USA) by Epoch Life Science (USA). The recombinant plasmid received from the company was transformed directly into competent E. coli BL21 (DES) expression host cells (Novagen, USA). Next day a single colony from the plate containing the recombinant plasmid was inoculated in 100 ml of Terrific broth and 25 ml of salt solution (TBS) containing 100 µg/ml of kanamycin and incubated overnight at 37° C., agitation at 180 rpm. Subsequently 50 µl of the overnight culture was inoculated into 500 ml TBS (450 ml Terrific broth+50 ml salt solution) with 100 µg/ml kanamycin and incubated at 37° C. with agitation at 200 rpm until the OD at 600 nm reached 0.4-0.6. Protein expression was induced by addition of 1 mM isopropyl β-D-1-thiogalactopyranoside (IPTG) to the culture for 4 hours at 30° C. The cells were harvested by centrifugation at 10,000×g, 4° C. for 10 min and the pellet kept at −80° C. On the following day, the pellet was resuspended in adequate volume of lysis buffer (1.5 v/w) containing a cocktail of protease inhibitors (Roche, Germany) and 0.5 mg/ml lysozyme and incubated for 30 min on ice. The cell suspension was then subjected to 5 min of sonication (30 sec on and 30 sec off), according to the instrument manual (Ultrasonic Liquid Pressor: Model XL2020, USA). After centrifugation at 10,000×g, 4° C. for 30 min, and the supernatant was transferred to a new tube and DNase (2500 ug/ml) was added and incubated on ice for another 15 min, followed by centrifugation of the tube at 10,000×g, 4° C. for 30 min. The resultant supernatant was filtered using a syringe filter (0.45 µm) and immediately mixed with Ni-NTA resin (Qiagen, USA), incubated at 4° C. (rotating) for 30 min, and the mixture was loaded into a chromatography column. Gradient washings were performed using 10 ml each of four kinds of washing buffers containing 500 mM NaCl (10 mM, 20 mM, 30 mM and 40 mM imidazole respectively). The protein fractions were eluted using elution buffer containing 250 mM imidazole. Protein-containing fractions from the affinity column were pooled and buffer exchanged with PBS containing 1 M urea (pH=7). The fractions were concentrated by centrifugation at 3000×g with a spin filter, then analysed by SDS-PAGE. The recombinant T. gondii RAP domain-containing protein was called rTgRA15.

Mass Spectrometry Analysis

A Coomassie blue-stained, sliced gel band of rTgRA15 was subjected to mass spectrometry analysis using a MALDI-TOF/TOF 5800 analyzer mass spectrometer (AB Sciex, Massachusetts, USA).

Western Blot of Recombinant Protein

Figure 7:
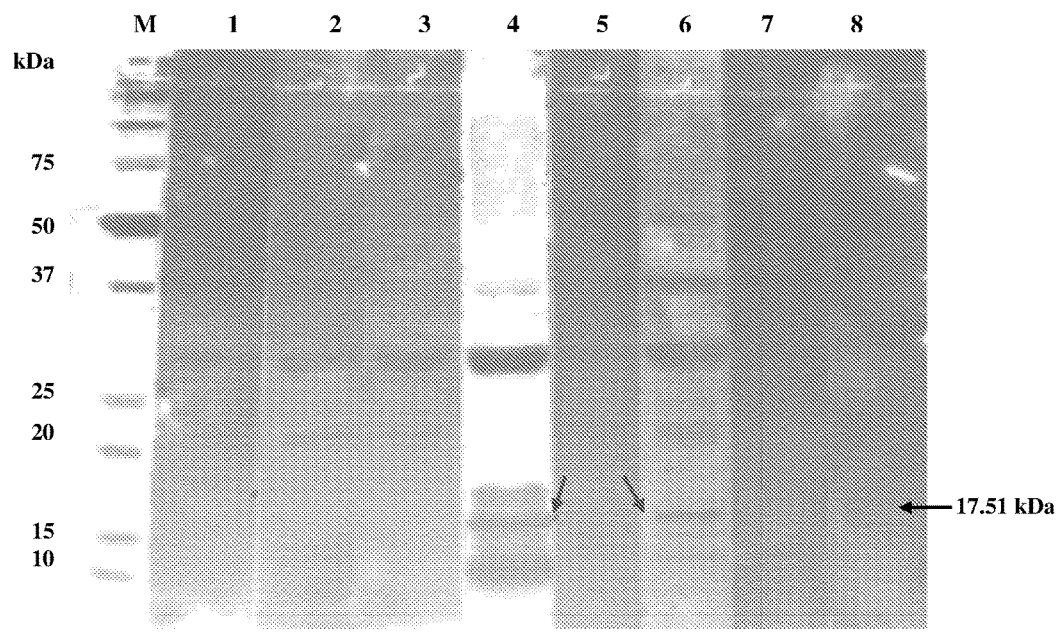
FIG. 7: Western blot of rTgRA15 antigen incubated with negative and positive serum samples to detect serum *Toxoplasma*-specific IgM. Strip M: low molecular weight, unstained marker; Strips 1-3: IgG– IgM–, serum samples from healthy people; Strip 4: positive control; Strip 5: negative control; Strip 6: IgM+ IgG+, low IgG avidity (acute serum sample); Strip 7-8: IgG+ IgM– (chronic serum samples).

After SDS-PAGE analysis, rTgRA15 was transferred onto the nitrocellulose membrane, then blocked with 1:5 dilution of Super Block™ solution (Thermo Scientific, USA). Next the membrane was washed with TBS-T washing buffer and incubated with anti-His-HRP at a 1:3000 dilution for 1 hour at room temperature. Western blots were also performed using human serum samples and anti-human IgM-HRP in order to determine the diagnostic sensitivity and specificity. Polypeptide rTgRA15 was run on SDS-PAGE and then transferred onto a nitrocelluose membrane. The membrane was blocked, washed and incubated with serum samples from healthy individuals (Strips 1-3: IgG− IgM−), patients with acute toxoplasmosis (Strip 6: IgM+ IgG+, low IgG avidity) and patients with chronic toxoplasmosis (Strips 7-8: IgM− IgG+). A washing step was performed, followed by incubation using anti-human IgM antibody conjugated to horseradish peroxidase. After another washing step, chemiluminescence substrate was added and developed on an X-ray film (FIG. 7). Strip 4 is a positive control, and strip 5 is a negative control. Lane 6 shows that patients with acute toxoplasmosis have serum antibodies directed to the rTgRA15 antigen.

Preparation of Lateral Flow Dipstick Dot Test

A Hi-flow Plus 90 membrane card (301 mm length) [Millipore, USA] was used and an absorbent pad was placed at the sticky part at the top of the membrane card so that there was a 2-3 mm overlap area between the nitrocellulose membrane on the card and the absorbent pad. The assembled membrane cared-absorbent pad was then cut into 5 mm dipstick strips using Index Cutter-I (A-Point Technologies, Minnesota, USA). A volume of 1 ul of rTgRA15 at various protein concentrations (1 mg/ml, 1.5 mg/ml, 2 mg/ml, 2.5 mg/ml) were dotted onto the dipsticks (one dot per dipstick). The dipsticks were placed for 2 hours in the incubator at 37° C. to dry. Next, the strips were blocked using western blocking solution (Roche, Germany) at dilution 1:10 and left to dry overnight in the incubator, then stored in a dry cabinet at room temperature.

Test Procedure

Using a 96-well plate, 10 µl of serum sample was diluted with 10 µl of PBS (1:2) and placed in a well. A volume of 25 µl of anti-human IgM conjugated to gold, diluted with PBS to OD 5.0 was placed in the adjacent well. A third well was filled with a volume of 30 µl chase buffer (PBS-T).

The dipstick was placed in the first well and the serum was allowed to flow upwards until it almost reached the edge of the absorbent pad. Then, the dipstick was placed in the second well containing the anti-human IgM conjugated to gold. Subsequently it was placed in the last well for washing, and then air dried. In a positive test result, a reddish dot was seen on the dipstick; while in a negative test result, no dot was seen on the dipstick. The whole test procedure until the result was obtained takes ~15-20 minutes.

Results

T. gondii Recombinant Antigen of Phage Clone AM15 Reacts with Serum from Subjects with Acute Toxoplasmosis.

At the final step of serum pre-adsorption, an OD value of 0.006 was observed for serum diluted at 1:100. In comparison, pooled non-adsorbed sera at the same dilution gave OD value of 3.34, thus this show that the pooled sera were exhaustively pre-adsorbed against T. gondii and E. coli XL1-Blue MRF' in-vitro antigens. FIG. 1 shows representative results of sensitivity and specificity evaluation of phage clone AM15.

*T. gondii* Recombinant Antigen is a RAP (RNA Associated Protein) Domain-Containing Protein.

The sequence of clone AM15 (SEQ ID NO: 1; shown in FIG. 2) was analyzed using the BLAST program at the Genbank and the *Toxoplasma* Genomic Resource (ToxoDB) databases, it was identified with 100% homology as TGME49_269830; a *T. gondii* ME49 protein coding gene on TGME49_chrVIII from 5,586,338 to 5,589,238 (Chromosome: VIII) that codes for RAP (RNA Associated Protein) domain-containing protein. The Genbank Accession ID No. is 7895000. It is also 100% similar to TGGT1_269830 and TGVEG_017050. TGME49, TGGT1 and TGVEG are three strains of *T. gondii* with genome sequences available in ToxoDB.

FIG. 3 shows the amino acid sequence SEQ ID NO: 2 of the in vivo-induced *T. gondii* RAP (RNA Associated Protein) domain-containing protein, designated rTgRA15 encoded by clone AM15.

FIG. 4 shows the nucleic acid sequence SEQ ID NO: 3, which encodes the full-length *T. gondii* RAP containing domain protein, with the position of the DNA insert of clone AM15 within that nucleic acid sequence highlighted and underlined. The predicted protein sequence encoded by the TGME_269830 gene is shown in FIG. 5 as SEQ ID NO: 4, again with the position of the recombinant antigen rTgRA15 highlighted and underlined.

*T. gondii* Recombinant Antigen of Phage Clone AM15 is Induced In-Vivo During Acute Toxoplasmosis.

Real time PCR was performed at annealing temperatures of 60° C. The levels of IVIAT-identified gene (TGME_269830) expression in-vivo relative to the levels of in-vitro gene expression in tachyzoites are shown in Table 2.

TABLE 2

Expression levels of TGME_269830 in-vivo relative to the level of its in-vitro expression in *T. gondii* tachyzoites.

| In-vivo Ct value | Average of in-vivo Ct value | ΔCt in-vivo | In-vitro Ct value | Average of in-vitro Ct value | ΔCt in-vivo | ΔΔCt value | Fold change |
|---|---|---|---|---|---|---|---|
| 33.85 | 34.75 | 11.15 | 45 | 45 | 21.4 | −10.25 | 1217.7 |
| 34.65 | | | No expression | | | | |
| 35.76 | | | No expression | | | | |

The data showed that the gene is expressed in-vivo but not in-vitro, with a 1217 fold difference in expression levels.

AM15 Phage React to IgM in Serum Samples from Subjects with Toxoplasmosis.

Table 3 shows a summary of the results for the initial diagnostic sensitivity and specificity evaluation of rTgRA15 antigen expressed by clone AM15 by phage immunoblot.

TABLE 3

Reactivity of recombinant phage immunoblot using rTgRA15

| No | Category of serum samples | No of samples | Positive result | Negative result |
|---|---|---|---|---|
| 1 | IgM+ IgG+, low IgG avidity | 10 | 10 | 0 |
| 2 | IgM+ IgG+, high IgG avidity | 8 | 8 | 0 |
| 3 | IgM− IgG−, healthy people | 10 | 0 | 10 |

Diagnostic sensitivity to detect specific IgM was based on Groups 1 & 2 serum samples: 18/18=100%. Diagnostic specificity was based on Group 3 serum samples: 10/10=100% rTgRA15 Protein is Sensitive to Detect *T. gondii*-Specific IgM on Western Blot

Figure 6:
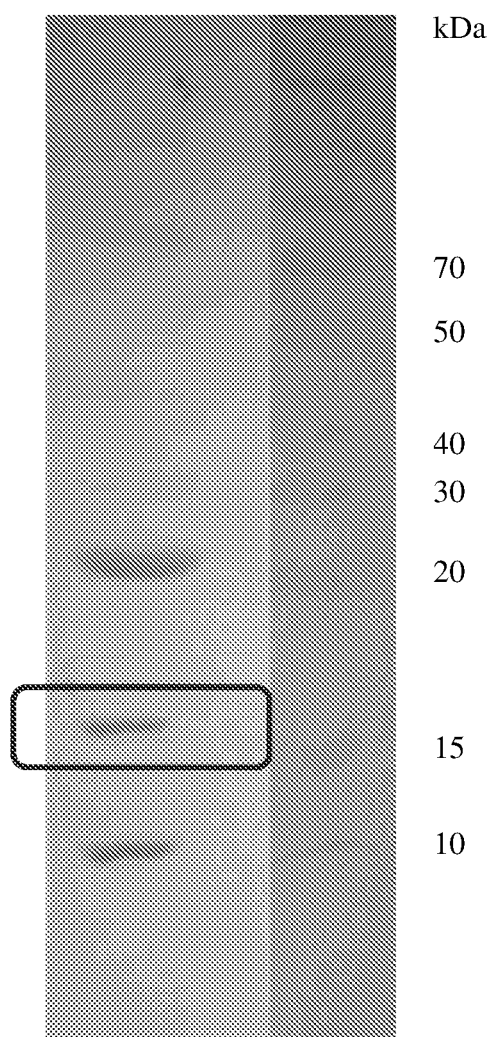
FIG. 6: SDS-PAGE profile of rTgRA15 antigen, derived from expression of the AM15 clone represented by SEQ ID NO: 1.

MALDI-TOF-TOF results searched against ToxoDB reaffirmed that the rTgRA15 protein was 100% homologous to a *T. gondii* RAP domain-containing protein, with protein scores (>200) and peptide scores well above the cut-off values. FIG. 6 shows an SDS-PAGE profile of proteins from recombinant bacteria culture expressing rTgRA15, where rTgRA15 is identified as having a molecular weight of approximately 17.5 kDa. A representative western blot, of rTgRA15 probed with sera from patients and controls to detect whether *T. gondii*-specific antibodies were present in the sera, is shown in FIG. 7. A summary of the results for diagnostic sensitivity and specificity evaluation of rTgRA15 is shown in Table 4.

TABLE 4

Diagnostic sensitivity and specificity of Western blot using rTgRA15

| No | Category of serum samples based on *Toxoplasma* serology using Platelia kits (BioRad, USA) | No of samples | Positive result | Negative result |
|---|---|---|---|---|
| 1 | IgM+ IgG+, low IgG avidity | 5 | 5 | 0 |
| 2 | IgM+ IgG+, high IgG avidity | 10 | 10 | 0 |
| 3** | IgM− IgG+ | 19 | 0 | 19 |
| 4 | IgM− IgG−, healthy people | 18 | 1 | 17 |
| 5 | IgM− IgG−, other infections | 12 | 0 | 12 |

Diagnostic sensitivity to detect specific IgM was based on Groups 1 & 2 serum samples: 15/15=100%. Diagnostic specificity was based on Groups 4, 5 serum samples: 29/30=96.6%. **Group 3 cannot be used to calculate either diagnostic sensitivity or specificity since they were serum samples from chronically infected people. For chronic infection, whether IgM is truly positive or negative will very much depend on the sensitivity of the detection test used;

thus with another test with higher sensitivity (than used in this study) some samples from Group 3 may be IgM+, IgG+.

The good diagnostic sensitivity (100%) and specificity (96.6%) showed that the rTgRA15 reacted with positive serum samples; and did not react with negative serum samples from healthy people and from other infections.

rTgRA15 Protein is Sensitive to Detect *T. Gondii*-Specific IgM on Lateral Flow Dipstick Dot Test The results of the diagnostic evaluation of dipstick dot test using rTgRA15 are summarized in Table 5.

TABLE 5

Diagnostic sensitivity and specificity of dipstick dot test using rTgRA15

| No | Category of serum samples | No of samples | Positive result | Negative result |
|---|---|---|---|---|
| 1 | IgM+ IgG+, low IgG avidity | 20 | 20 | 0 |
| 2 | IgM+ IgG+, high IgG avidity | 10 | 10 | 0 |
| 3** | IgM− IgG+, | 11 | 5 | 6 |
| 4 | IgM− IgG−, healthy people | 18 | 0 | 18 |
| 5 | IgM− IgG−, other infections | 10 | 1 | 9 |

Diagnostic sensitivity to detect specific IgM was based on Groups 1 & 2 serum samples: 30/30=100%. Diagnostic specificity was based on Groups 4 & 5 serum samples: 27/28=96.4%. **Group 3 cannot be used to calculate either diagnostic sensitivity or specificity since they were serum samples from chronically infected people. For chronic infection, whether IgM is truly positive or negative will very much depend on the sensitivity of the detection test used; thus with another test with higher sensitivity (than used in this study) some samples from Group 3 may be IgM+, IgG+.

Figure 8:
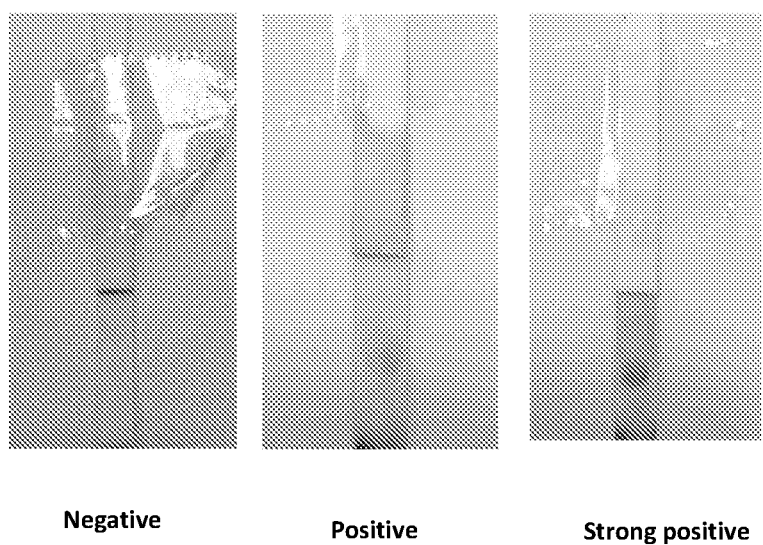
FIG. 8: Representative dipstick dot test using rTgRA15 antigen probed with serum from toxoplasmosis or control subjects. *Toxoplasma*-specific serum IgM binding is detected with gold-conjugated anti-human IgM antibody.

Thirty-six serum samples from patients with acute toxoplasmosis tested positive (100% sensitivity), these comprised 10 samples were from high-IgG avidity sera and twenty from low-IgG avidity sera. Twenty-seven out of 28 serum samples from healthy people and those with other infections tested negative with the dipstick i.e. 96.4% specificity. Representative images of dipstick dot test results are shown in FIG. 8.

We have shown experimentally that rTgRA15 is a good diagnostic protein for sensitive and specific detection of human anti-*T. gondii* IgM antibody, both by Western blot and dipstick dot test. Thus this protein and/or isolated or recombinant antibodies specific for the protein are of value, especially for testing of subjects for toxoplasmosis.

Moreover, since rTgRA15 is an in-vivo induced antigen which shows almost exclusive expression in in-vivo grown *T. gondii* and almost no expression in in-vitro grown *T. gondii*, it is also potentially very useful to be used in a vaccine and as a therapeutic target according to known methods (Handfield et al., *Trends Microbiol* 2000; 8: 336-39; John et al., *Infection and Immunity* 2005; 73: 2665-79; Hongwei et al., *BMC Microbiol*, 2009; 9: 201; Lowry et al., *Plos One*, 2011; 6 (3): e17425, incorporated herein by reference).

REFERENCES

1. Amerizadeh, A., Idris, Z. M., Khoo, B. Y., Kotresha, D., Yunus, M. H., Abdul Karim, I. Z., Saadatnia, G., Teh, A. Y., Noordin, R: Identification of *Toxoplasma gondii* in-vivo induced antigens by cDNA library immunoscreening with chronic toxoplasmosis sera. *Microb Pathog.* 2013a; 54: 60-66.
2. Amerizadeh, A., Khoo, B. Y., Teh, A. Y., Golkar, M., Abdul Karim, I. Z., Osman, S., Yunus, M. H., Noordin, R. Identification and real-time expression analysis of selected *Toxoplasma gondii* in-vivo induced antigens recognized by IgG and IgM in sera of acute toxoplasmosis patients. *BMC Infectious Disease* 2013b; 13: 287-299.
3. Angelichio, M. J., and Camilli, A. In vivo expression technology. *Infection and Immunity* 2002; 70: 6518-6523.
4. Chen, G., et al., Protective effect of DNA-mediated immunization with a combination of SAG1 and IL-2 gene adjuvant against infection of *Toxoplasma gondii* in mice. *Chin Med J* (Engl), 2002; 115(10): 1448-52.
5. Costa-Silva, T. A., et al., Evaluation of immunization with tachyzoite excreted-secreted proteins in a novel susceptible mouse model (A/Sn) for *Toxoplasma gondii*. *Exp Parasitol,* 2008; 120(3): 227-34.
6. Handfield, M., Brady, L. J., Progulske-Fox, A., Hillman, J. D. IVIAT: a novel method to identify microbial genes expressed specifically during human infections. *Trends Microbiol* 2000; 8: 336-39.
7. Hensel, M., Shea, J. E., Gleeson, C., Jones, M. D., Dalton E., Holden, D. W. Simultaneous identification of bacterial virulence genes by negative selection. *Science*, 1995; 269: 400-403.
8. Hongwei, G., Haodan, Z., Chengping, L. Use of in vivo-induced antigen technology (IVIAT) for the identification of *Streptococcus suis* serotype 2 in vivo-induced bacterial protein antigens. *BMC Microbiol,* 2009; 9: 201.
9. Lowry J E, Isaak D D, Leonhardt J A, Vernati G, Pate J C, Andrews G P. Vaccination with *Brucella abortus* Recombinant In Vivo-Induced Antigens Reduces Bacterial Load and Promotes Clearance in a Mouse Model for Infection. *Plos One,* 2011; 6 (3): e17425.
10. Jenum P A, Stray-Pedersen B. Development of specific immunoglobulins G, M, and A following primary *Toxoplasma gondii* infection in pregnant women. *J Clin Microbiol,* 1998 October; 36(10): 2907-13.
11. John M, Kudva I T, Griffin R W, Dodson A W, McManus B, Krastins B, Sarracino D, Progulske-Fox A, Hillman J D, Handfield M, Tarr P I, Calderwood S B. Use of in vivo-induced antigen technology for identification of *Escherichia coli* O157:H7 proteins expressed during human infection. *Infection and Immunity* 2005; 73: 2665-79.
12. Jongert, E., et al., An enhanced GRA1-GRA7 cocktail DNA vaccine primes anti-*Toxoplasma* immune responses in pigs. *Vaccine* 2008; 26(8): 1025-31.
13. Khan A, Taylor S, Su C, Mackey A J, Boyle J, Cole R, Glover D, Tang K, Paulsen I T, Berriman M, Boothroyd J C, Pfefferkon E R, Dubey J P, Ajioka J W, Roos D S, Wootton J C, Sibely L D: Composite genome map and recombination parameters derived from three archetypal lineages of *Toxoplasma gondii*. *Nucleic Acids Res* 2005; 33: 2980-92.
14. Livak K J, Schmittgen T D: Analysis of relative gene expression data using real-time quantitative PCR and the 2-ΔΔCT method. *Methods* 2001; 25: 402-8.
15. Letscher-Bru, V., et al., Vaccination with *Toxoplasma gondii* SAG-1 protein is protective against congenital toxoplasmosis in BALB/c mice but not in CBA/J mice. *Infect Immun* 2003; 71(11): 6615-9.
16. Lopez A, Dietz V J, Wilson M, Navin T R, Jones J L. Preventing congenital toxoplasmosis. *MMWR Recomm Rep* 2000 Mar. 31; 49(RR-2): 59-68.
17. Murat J B, Hidalgo H F, Brenier-Pinchart M P, Pelloux H. Human toxoplasmosis: which biological diagnostic 18. Nissapatorn V, Abdullah K A. Review on human toxoplasmosis in Malaysia: the past, present and prospective future. *Southeast Asian J Trop Med Public Health* 2004; March 35(1): 24-30.
19. Nutter F B, Dubey J P, Levine J, Breitschwerdt E B, Ford R B, Stoskopf M K. Seroprevalences of antibodies against *Bartonella henselae* and *Toxoplasma gondii* and fecal shedding of *Cryptosporidium* spp, *Giardia* spp, and *Toxocara cati* in feral and pet domestic cats. *JAMA* 2004; 229: 1394-1398.
20. Ramachandran, N., Hainsworth, E., Bhullar, B., Eisenstein, S., Rosen, B., Lau, A. Y., et al. Self-assembling protein microarrays. *Science* 2004; 305: 86-90.
21. Remington J S, Mc Leod R, Wilson C B, Desmonts G: Toxoplasmosis. In Infectious diseases of the fetus and newborn infant. 7th edition. Edited by Remington J S, Klein J O, Wilson C B, Nizet V, Maldonado Y A. Pennsylvania: Elsevier Saunders; 2011: 915-1041.
22. Sambrook and Russell, Molecular Cloning: A Laboratory Manual, Cold Springs Harbor Laboratory, New York (2001)
23. Tan H K, Schmidt D, Stanford M, Tear-Fahnehjelm K, Ferret N, Salt A, Gilbert R, et al. Risk of visual impairment in children with congenital toxoplasmic retinochoroiditis. *Am J Ophthalmol* 2007; 144: 48-653.
24. Torgerson P R, Mastroiacovo P. The global burden of congenital toxoplasmosis: a systematic review. *Bull World Health Organ* 2013 Jul. 1; 91(7): 501-8.
25. Valdivia, R. H., and Falkow, S. Fluorescence-based isolation of bacterial genes expressed within host cells. *Science* 1997; 277: 2007-2011.
26. Wastling, J. M., D. Harkins, and D. Buxton, Western blot analysis of the IgG response of sheep vaccinated with S48 *Toxoplasma gondii* (Toxovax). *Res Vet Sci* 1994; 57(3): 384-6
27. Zhao, G., et al., Identification and characterization of *Toxoplasma gondii* aspartic protease 1 as a novel vaccine candidate against toxoplasmosis. *Parasit Vectors* 2013; 6: 175.

What is claimed is:

1. A method of detecting *T. gondii* in a biological sample, comprising the steps of:
   a) providing at least one biological sample; and
   b) i) contacting the at least one biological sample with an antigen, wherein the antigen is an isolated or recombinant *T. gondii* RAP domain-containing protein comprising the amino acid sequence shown in SEQ ID NO: 2 or SEQ ID NO: 4 or an antigenic fragment thereof; and detecting specific and selective antigen-antibody binding between saki antigen and *T. gondii*-specific antibody, wherein the binding indicates the presence of *T. gondii* in the sample; or
   ii) detecting the presence of *T. gondii* RAP domain-containing protein, or nucleic acid molecule encoding same which comprises the sequence shown in SEQ ID NO: 1 or SEQ ID NO: 3, in the biological sample, wherein the detection of the RAP domain-containing protein or nucleic acid molecule in the biological sample constitutes detection of *T. gondii*.

2. The method according to claim 1, wherein the RAP domain-containing protein is detected with an antibody that specifically and selectively binds the protein, and the nucleic acid molecule is detected using nucleic acid amplification.

3. The method according to claim 1, wherein the RAP domain-containing protein is detected using immunoassay.

4. A method of detecting whether a subject has toxoplasmosis,
   comprising the steps;
   a) contacting a sample from the subject with an antigen, wherein the antigen is an isolated or recombinant *T. gondii* RAP domain-containing protein comprising the amino acid sequence shown in SEQ ID NO: 2 or SEQ ID NO: 4 or an antigenic fragment thereof, and detecting specific and selective antibody-antigen binding, wherein the binding indicates the presence of *T. gondii*-specific antibodies and toxoplasmosis in the subject; or
   b) detecting the presence of *T. gondii* RAP domain-containing protein, or nucleic acid molecule encoding same which comprises the sequence shown in SEQ ID NO: 1 or SEQ ID NO: 3, in a sample from the subject, wherein the detection of the RAP domain-containing protein or nucleic acid molecule in the sample indicates the presence of toxoplasmosis.

5. The method according to claim 4, wherein the *T. gondii*-specific antibodies are IgM antibodies.

6. A method of treatment or prophylaxis of toxoplasmosis, comprising administering to a subject an efficacious amount of a vaccine comprising at least one *T. gondii* RAP domain-containing protein or antigenic fragment thereof, wherein the RAP domain-containing protein comprises the amino acid sequence shown in SEQ ID NO: 2 or SEQ ID NO: 4.

7. The method according to claim 1, wherein *Toxoplasma* is indicated by specific and selective binding of the protein to *T. gondii*-specific IgM antibodies present in the biological sample isolated from the subject.

8. A method of treating toxoplasmosis in a subject in need thereof, comprising administering to the subject at least one *T. gondii* RAP domain-containing protein comprising the amino acid sequence shown in SEQ ID NO: 2 or SEQ ID NO: 4 or an antigenic fragment thereof.

* * * * *